United States Patent
Alvarez de Toledo et al.

(10) Patent No.: US 6,562,024 B2
(45) Date of Patent: *May 13, 2003

(54) DRAINAGE CATHETER DELIVERY SYSTEM

(75) Inventors: Fernando Alvarez de Toledo, Concord, MA (US); Michael Ciannella, Marlborough, MA (US); Susan M. Ostrowski, Arlington, MA (US); Albert N. Solbjor, Waltham, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 46 days.

This patent is subject to a terminal disclaimer.

(21) Appl. No.: 09/854,088

(22) Filed: May 11, 2001

(65) Prior Publication Data

US 2001/0018574 A1 Aug. 30, 2001

Related U.S. Application Data

(63) Continuation of application No. 09/312,341, filed on May 14, 1999, now Pat. No. 6,248,100, which is a continuation-in-part of application No. 09/257,764, filed on Feb. 25, 1999, now Pat. No. 6,264,624, which is a continuation of application No. 08/911,323, filed on Aug. 14, 1997, now Pat. No. 5,921,952.

(51) Int. Cl.[7] .............................................. A61M 1/00
(52) U.S. Cl. ........................... 604/540; 604/8; 604/544; 604/523
(58) Field of Search ................. 604/540, 264, 604/523, 541, 543, 544, 528, 500, 514, 517, 515, 93.01, 103.04, 164.13, 8, 524, 530–532, 104, 105–107; 623/1.11, 23.64, 23.66, 23.7; 600/585, 29, 114, 30, 433–435; 606/191

(56) References Cited

U.S. PATENT DOCUMENTS

| | | | |
|---|---|---|---|
| 2,212,334 A | 8/1940 | Wallerich | 18/58 |
| 2,393,003 A | 1/1946 | Smith | 128/349 |
| 3,100,490 A | 8/1963 | Desautels | 128/350 |
| 3,332,424 A | 7/1967 | Minteer | 128/349 |
| 3,421,509 A | 1/1969 | Fiore | 128/349 |
| 3,592,197 A | 7/1971 | Cohen | 128/349 |
| 3,783,453 A | 1/1974 | Bolie | 3/1 |
| 3,908,635 A | 9/1975 | Viek | 128/2 M |
| 3,938,529 A | 2/1976 | Gibbons | 128/349 R |
| 3,995,642 A | 12/1976 | Adair | 128/349 R |
| 4,212,304 A | 7/1980 | Finney | 128/349 R |
| 4,225,979 A | 10/1980 | Rey et al. | 3/1 |

(List continued on next page.)

FOREIGN PATENT DOCUMENTS

| | | |
|---|---|---|
| CA | 1112119 A | 11/1981 |
| DE | 3345612 A1 | 6/1985 |
| DE | 3919740 A1 | 12/1990 |
| GB | 2 018 600 A | 10/1979 |
| WO | WO 93/00126 A1 | 1/1993 |
| WO | WO 99/08740 | 2/1999 |

*Primary Examiner*—Brian L. Casler
*Assistant Examiner*—Cris L. Rodriguez
(74) *Attorney, Agent, or Firm*—Crompton, Seager & Tufte, LLC

(57) ABSTRACT

A single operator drainage catheter delivery system and method of use. The delivery system includes a guide member having a guidewire lumen extending through a distal portion thereof, with a proximal guidewire port located distal of the proximal end. A placement catheter disposed over the guide member has a catheter lumen extending through a distal portion thereof, with a proximal guidewire port located distal of the proximal end. Locating the proximal guidewire ports as such allows the delivery system to be used by a single person with a shorter guidewire. A drainage catheter is disposed about the guide member distal of the placement catheter. The drainage catheter delivery system preferably includes a means for releasably connecting the placement catheter to the drainage catheter, wherein the releasable connecting means disconnects the drainage catheter upon displacement of the guide member.

23 Claims, 15 Drawing Sheets

U.S. PATENT DOCUMENTS

| | | | |
|---|---|---|---|
| 4,242,304 A | 12/1980 | Ryder | 422/119 |
| 4,248,214 A | 2/1981 | Hannah et al. | 128/7 |
| 4,307,723 A | 12/1981 | Finney | 128/349 R |
| 4,334,327 A | 6/1982 | Lyman et al. | 3/1 |
| 4,382,445 A | 5/1983 | Sommers | 604/8 |
| 4,434,797 A | 3/1984 | Silander | 128/343 |
| 4,474,569 A | 10/1984 | Newkirk | 604/8 |
| 4,484,585 A | 11/1984 | Baier | 128/748 |
| 4,500,313 A | 2/1985 | Young | 604/280 |
| 4,531,933 A | 7/1985 | Norton et al. | 604/8 |
| 4,545,373 A | 10/1985 | Christoudias | 128/303 R |
| 4,568,338 A | 2/1986 | Todd | 604/281 |
| 4,592,341 A | 6/1986 | Omagari et al. | 128/4 |
| 4,610,657 A | 9/1986 | Densow | 604/8 |
| 4,643,716 A | 2/1987 | Drach | 604/8 |
| 4,645,493 A | 2/1987 | Ferrando et al. | 604/174 |
| 4,671,795 A | 6/1987 | Mulchin | 604/281 |
| 4,684,369 A | 8/1987 | Wildemeersch | 604/272 |
| 4,699,611 A | 10/1987 | Bowden | 604/51 |
| 4,713,049 A | 12/1987 | Carter | 604/8 |
| 4,738,667 A | 4/1988 | Galloway | 604/281 |
| 4,747,833 A | 5/1988 | Kousai et al. | 604/164 |
| 4,755,175 A | 7/1988 | Nilsson | 604/268 |
| 4,762,128 A | 8/1988 | Rosenbluth | 128/343 |
| 4,783,454 A | 11/1988 | Liu | 514/214 |
| 4,784,651 A | 11/1988 | Hickey | 604/282 |
| 4,787,884 A | 11/1988 | Goldberg | 604/8 |
| 4,790,809 A | 12/1988 | Kuntz | 604/8 |
| 4,790,810 A | 12/1988 | Pugh, Jr. et al. | 604/8 |
| 4,813,925 A | 3/1989 | Anderson, Jr. et al. | 604/8 |
| 4,820,262 A | 4/1989 | Finney | 604/8 |
| 4,822,333 A | 4/1989 | Lavarenne | 600/30 |
| 4,824,435 A | 4/1989 | Giesy et al. | 604/49 |
| 4,832,055 A | 5/1989 | Palestrant | 128/899 |
| 4,874,360 A | 10/1989 | Goldberg et al. | 604/8 |
| 4,886,065 A | 12/1989 | Collins, Jr. | 128/642 |
| 4,913,141 A | 4/1990 | Hillstead | 606/108 |
| 4,913,683 A | 4/1990 | Gregory | 604/8 |
| 4,931,037 A | 6/1990 | Wetterman | 604/8 |
| 4,950,228 A | 8/1990 | Knapp, Jr. et al. | 604/8 |
| 4,955,858 A | 9/1990 | Drews | 604/8 |
| 4,957,479 A | 9/1990 | Roemer | 604/8 |
| 4,963,129 A | 10/1990 | Rusch | 604/8 |
| 4,973,301 A | 11/1990 | Nissenkorn | 604/8 |
| 4,990,133 A | 2/1991 | Solazzo | 604/8 |
| 4,994,066 A | 2/1991 | Voss | 606/108 |
| 5,019,085 A | 5/1991 | Hillstead | 606/108 |
| 5,019,102 A | 5/1991 | Hoene | 623/12 |
| 5,052,998 A | 10/1991 | Zimmon | 604/8 |
| 5,098,374 A | 3/1992 | Othel-Jacobsen et al. | 604/8 |
| 5,116,309 A | 5/1992 | Coll | 604/8 |
| 5,141,502 A | 8/1992 | Macaluso, Jr. | 604/281 |
| 5,147,370 A | 9/1992 | McNamara et al. | 606/108 |
| 5,152,749 A | 10/1992 | Giesy et al. | 604/164 |
| 5,160,341 A | 11/1992 | Brenneman et al. | 606/198 |
| 5,234,437 A | 8/1993 | Sepetka | 606/108 |
| 5,250,071 A | 10/1993 | Palermo | 606/198 |
| 5,261,916 A | 11/1993 | Engelson | 606/108 |
| 5,267,958 A | 12/1993 | Buchbinder et al. | 604/96 |
| 5,282,784 A | 2/1994 | Willard | 604/8 |
| 5,295,954 A | 3/1994 | Sachse | 604/8 |
| 5,304,195 A | 4/1994 | Twyford, Jr. et al. | 606/191 |
| 5,304,198 A | 4/1994 | Samson | 604/194 |
| 5,320,604 A | 6/1994 | Walker et al. | 604/96 |
| 5,322,501 A | 6/1994 | Mahmud-Durrani | 604/8 |
| 5,324,259 A | 6/1994 | Taylor et al. | 604/96 |
| 5,334,185 A | 8/1994 | Giesy et al. | 604/164 |
| 5,346,467 A | 9/1994 | Coll | 604/8 |
| 5,348,537 A | 9/1994 | Wiesner et al. | 604/96 |
| 5,354,263 A | 10/1994 | Coll | 604/8 |
| 5,364,340 A | 11/1994 | Coll | 604/8 |
| 5,364,354 A | 11/1994 | Walker et al. | 604/96 |
| 5,364,376 A | 11/1994 | Horzewski et al. | 604/280 |
| 5,372,600 A | 12/1994 | Beyar et al. | 606/108 |
| 5,391,155 A | 2/1995 | Sachse | 604/170 |
| 5,401,257 A | 3/1995 | Chevalier, Jr. et al. | 604/265 |
| 5,405,378 A | 4/1995 | Strecker | 623/1 |
| 5,407,435 A | 4/1995 | Sachse | 604/170 |
| 5,409,468 A | 4/1995 | Sachse | 604/282 |
| 5,454,788 A | 10/1995 | Walker et al. | 604/96 |
| 5,458,615 A | 10/1995 | Klemm et al. | 606/198 |
| 5,476,505 A | 12/1995 | Limon | 623/1 |
| 5,480,434 A | 1/1996 | Eckstein et al. | 623/11 |
| 5,484,409 A | 1/1996 | Atkinson et al. | 604/96 |
| 5,496,344 A | 3/1996 | Kanesaka et al. | 606/191 |
| 5,540,236 A | 7/1996 | Ginn | 128/772 |
| 5,578,009 A | 11/1996 | Kraus et al. | 604/96 |
| 5,599,291 A | 2/1997 | Balbierz et al. | 604/8 |
| 5,639,274 A | 6/1997 | Fischell et al. | 604/96 |
| 5,645,533 A | 7/1997 | Blaeser et al. | 604/164 |
| 5,653,748 A | 8/1997 | Strecker | 623/1 |
| 5,669,880 A | 9/1997 | Solar | 604/96 |
| 5,676,654 A | 10/1997 | Ellis et al. | 604/103 |
| 5,681,274 A | 10/1997 | Perkins et al. | 604/8 |
| 5,690,642 A | 11/1997 | Osborne et al. | 606/108 |
| 5,693,015 A | 12/1997 | Walker et al. | 604/96 |
| 5,776,099 A | 7/1998 | Tremulis | 604/96 |
| 5,921,952 A | 7/1999 | Desmond, III et al. | |
| 5,921,971 A * | 7/1999 | Agro et al. | 604/264 |
| 6,095,990 A * | 8/2000 | Parodi | 600/585 |
| 6,159,195 A * | 12/2000 | Ha et al. | 604/103.04 |
| 6,248,100 B1 | 6/2001 | de Toledo et al. | 604/540 |
| 6,264,624 B1 | 7/2001 | Desmond, III et al. | |

* cited by examiner

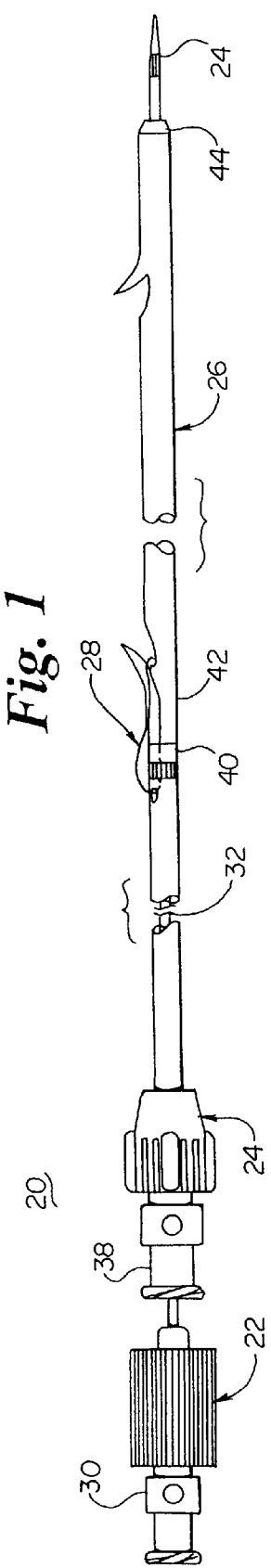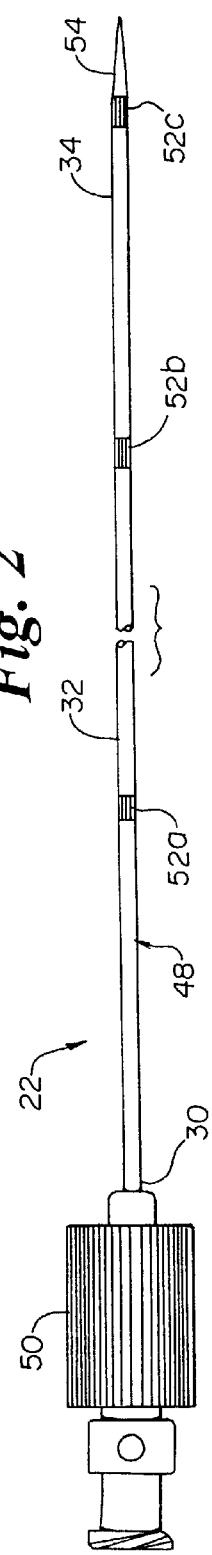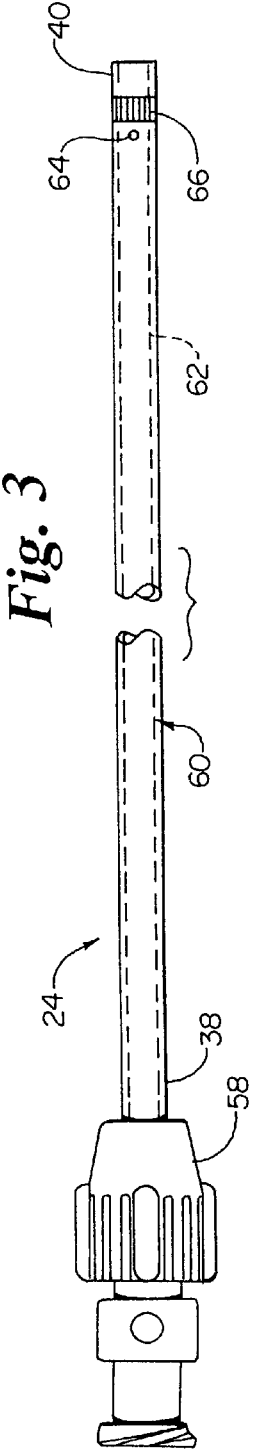

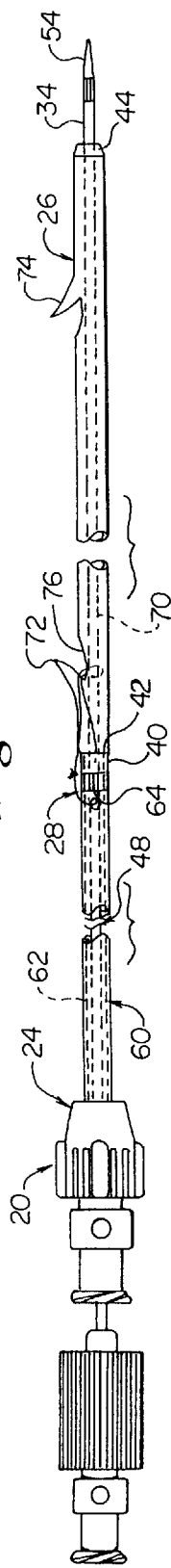
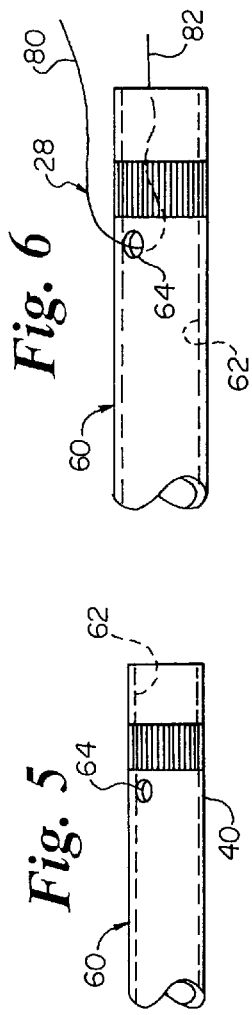
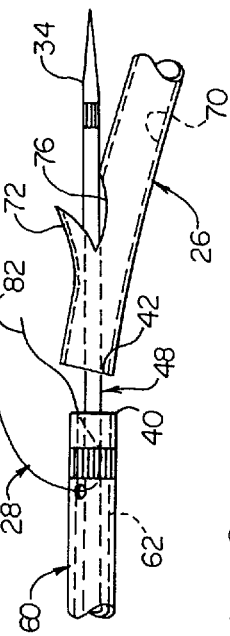
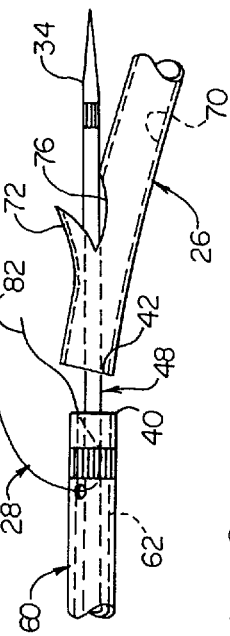
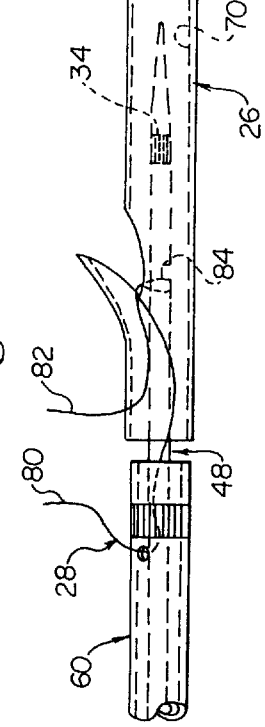

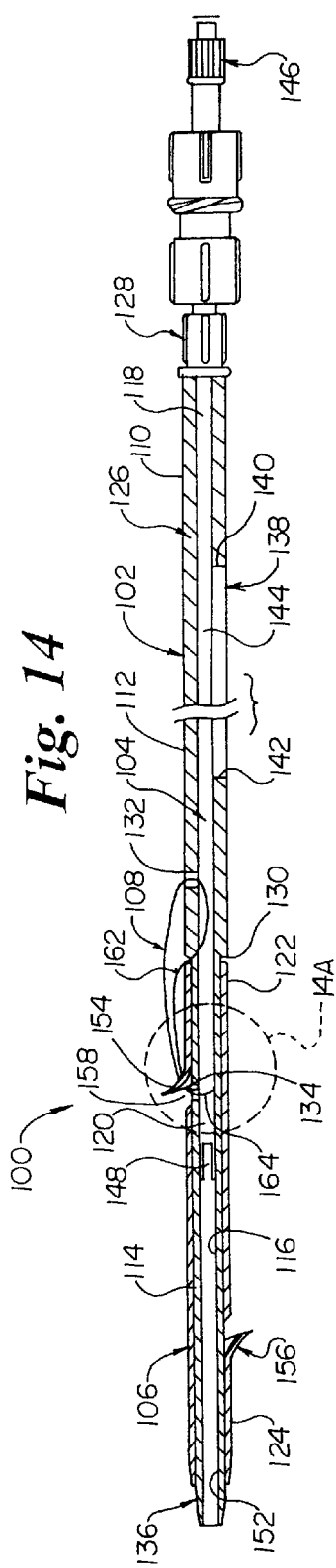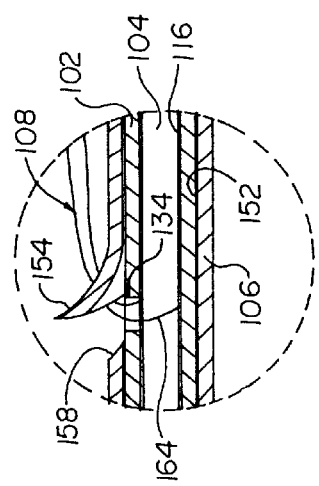
Fig. 14
Fig. 14A

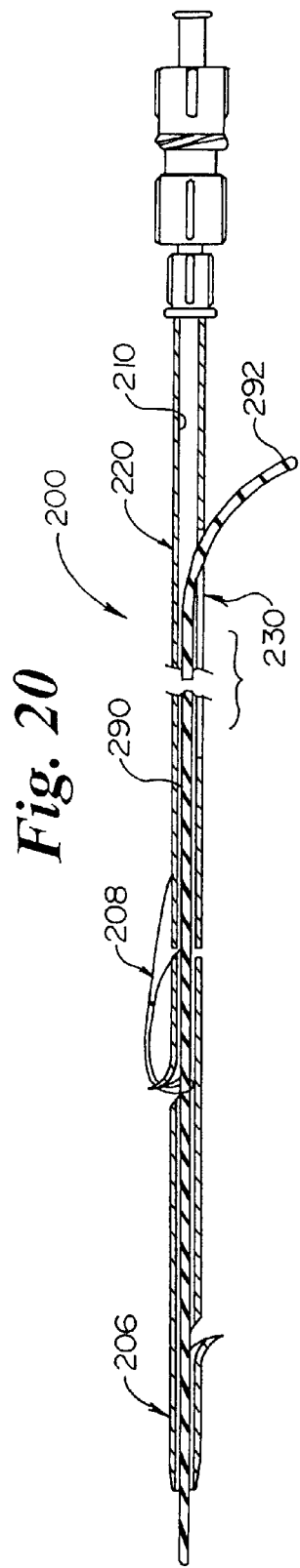
Fig. 20
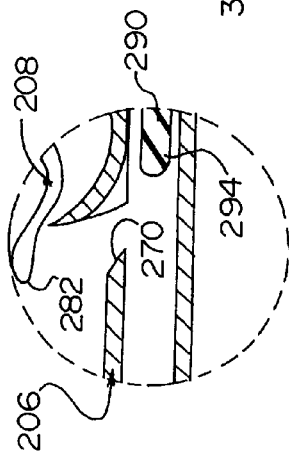
Fig. 21
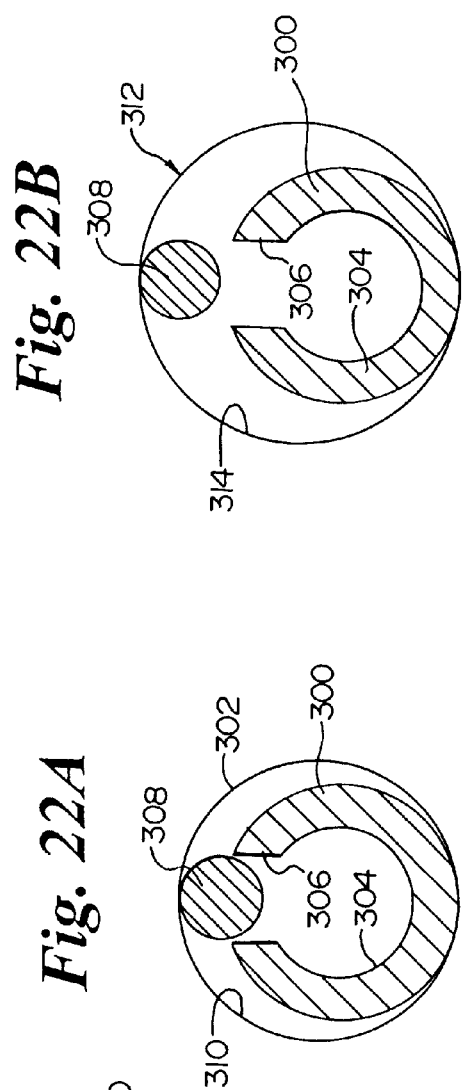
Fig. 22A
Fig. 22B

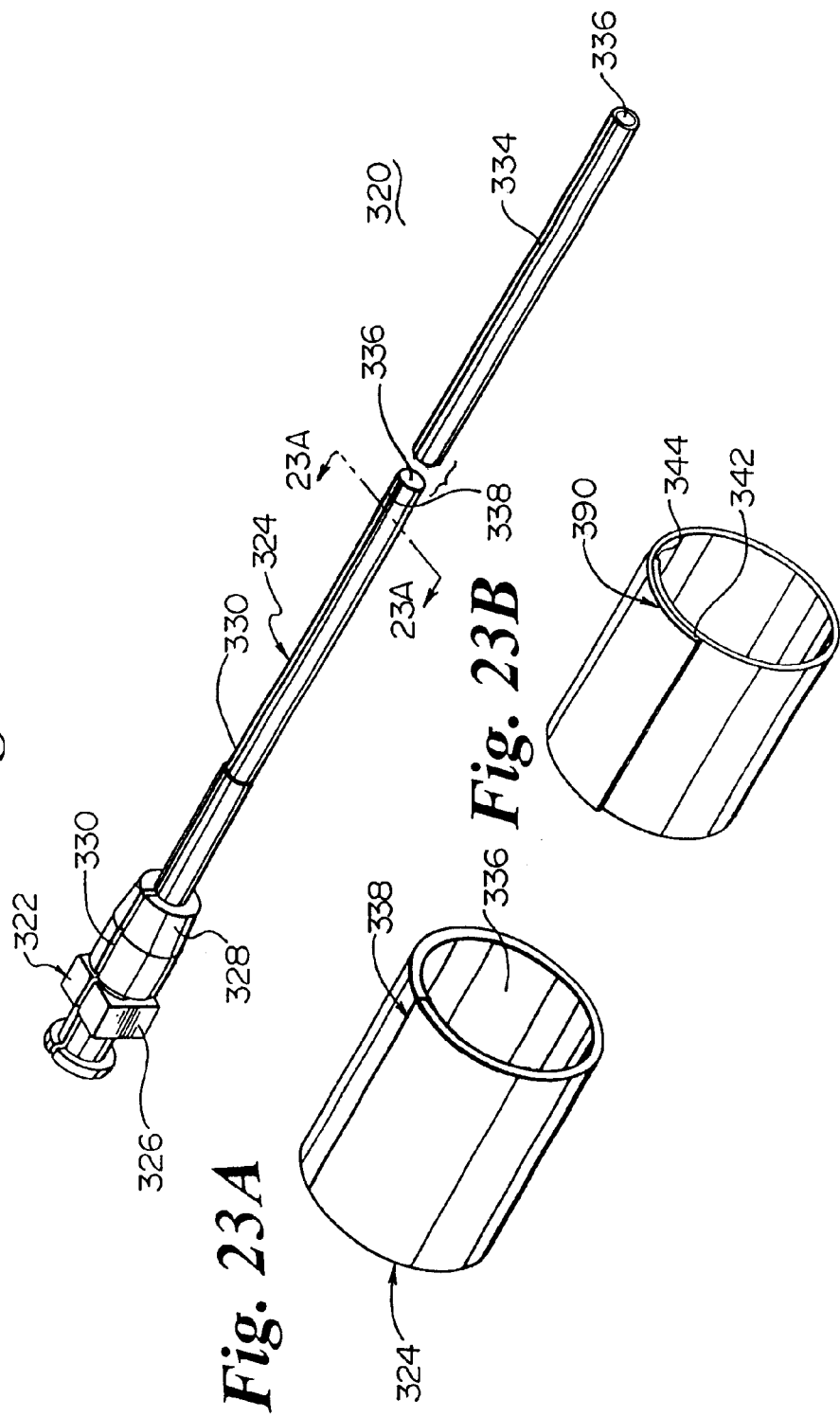

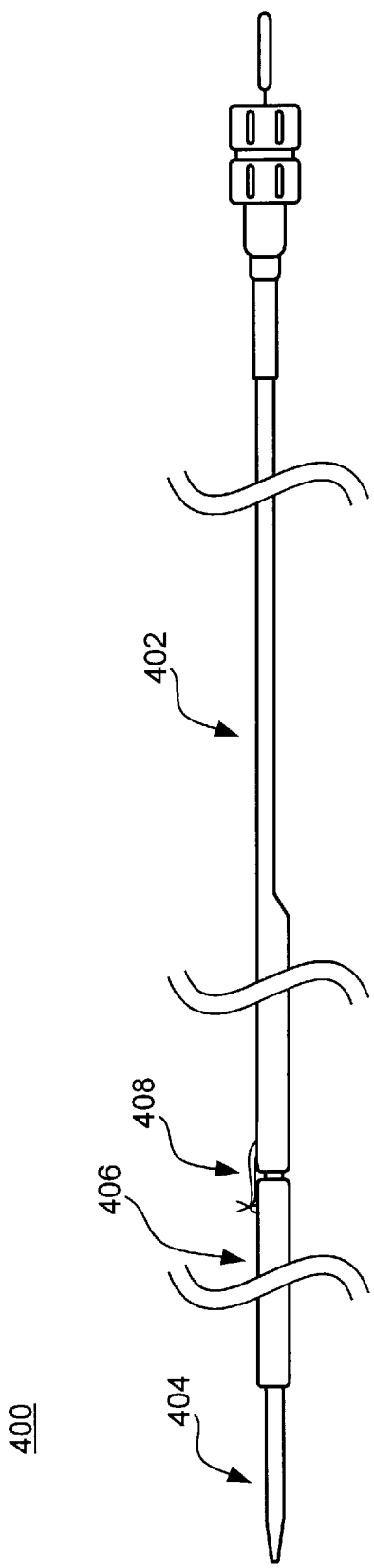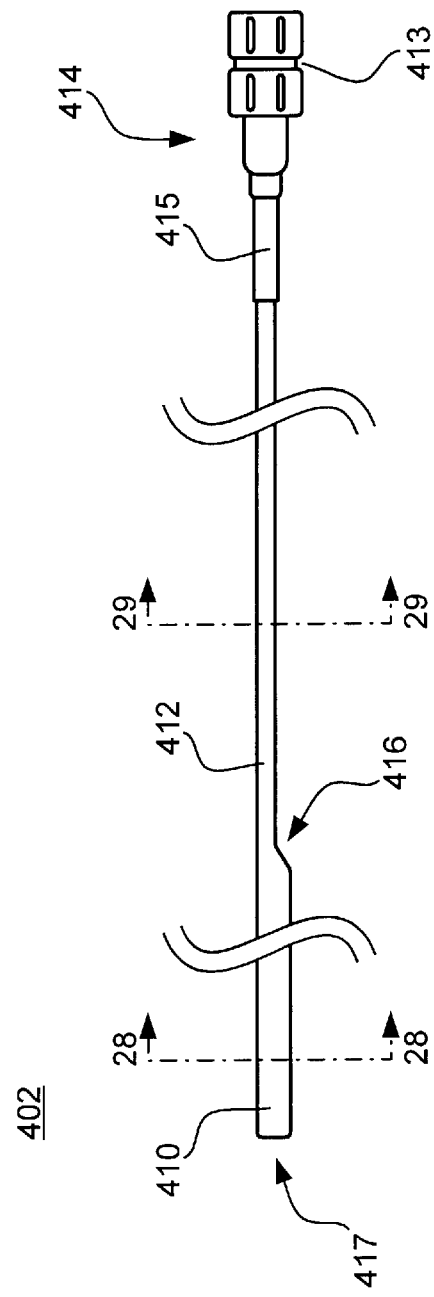

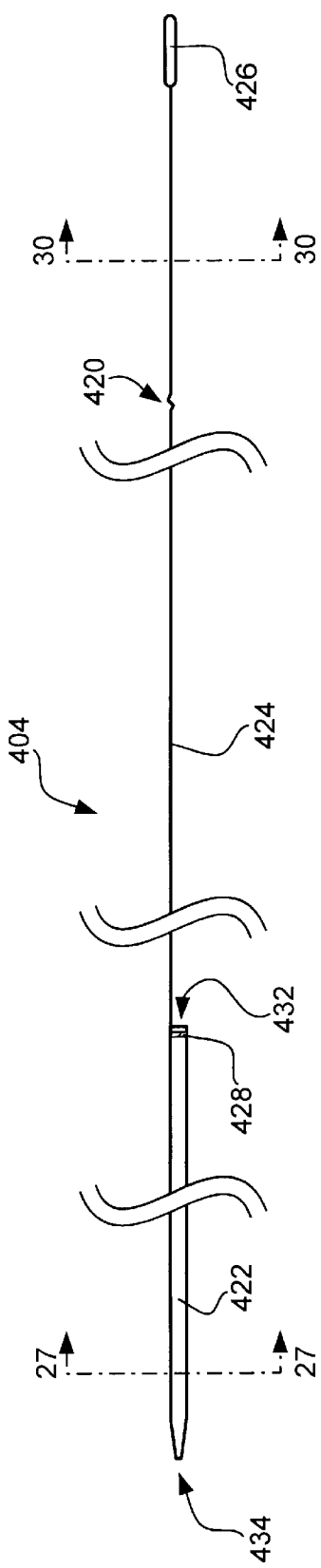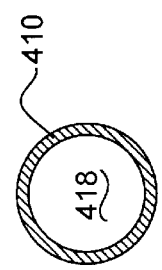
FIG. 26
FIG. 27
FIG. 28
FIG. 29
FIG. 30

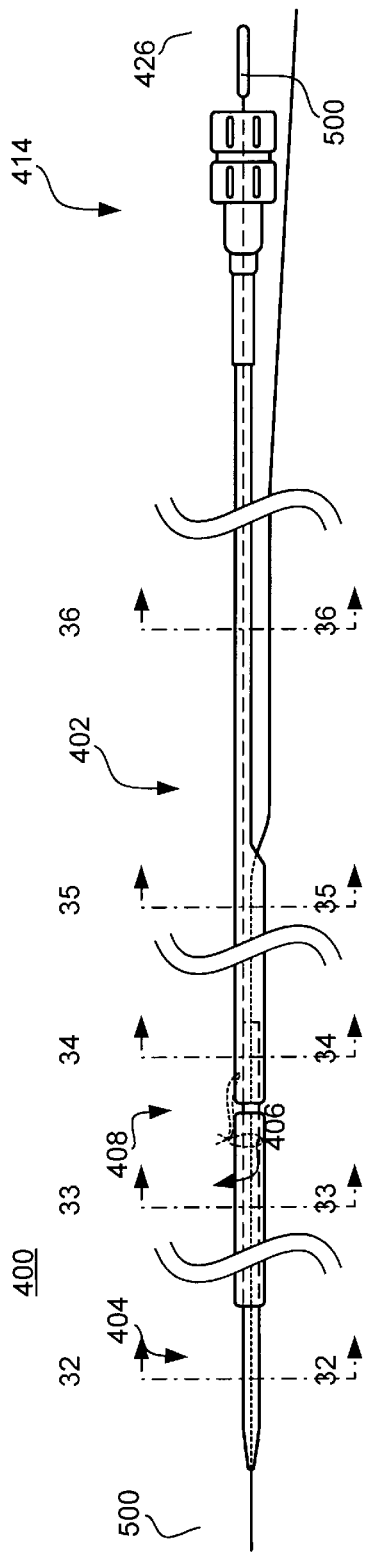
FIG. 31
FIG. 32
FIG. 33
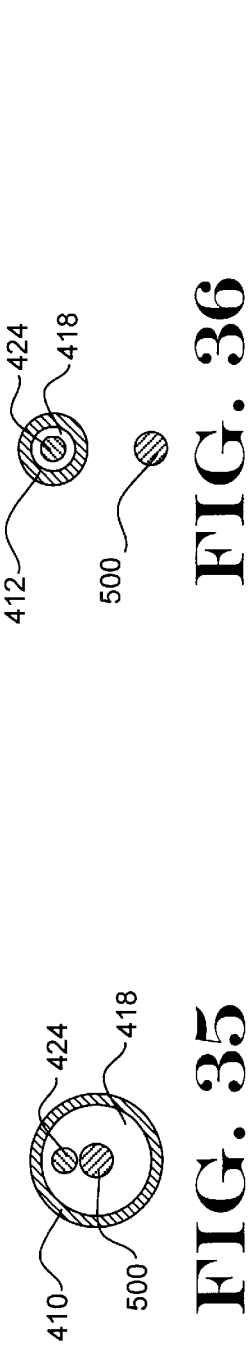
FIG. 34
FIG. 35
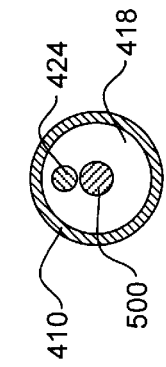
FIG. 36

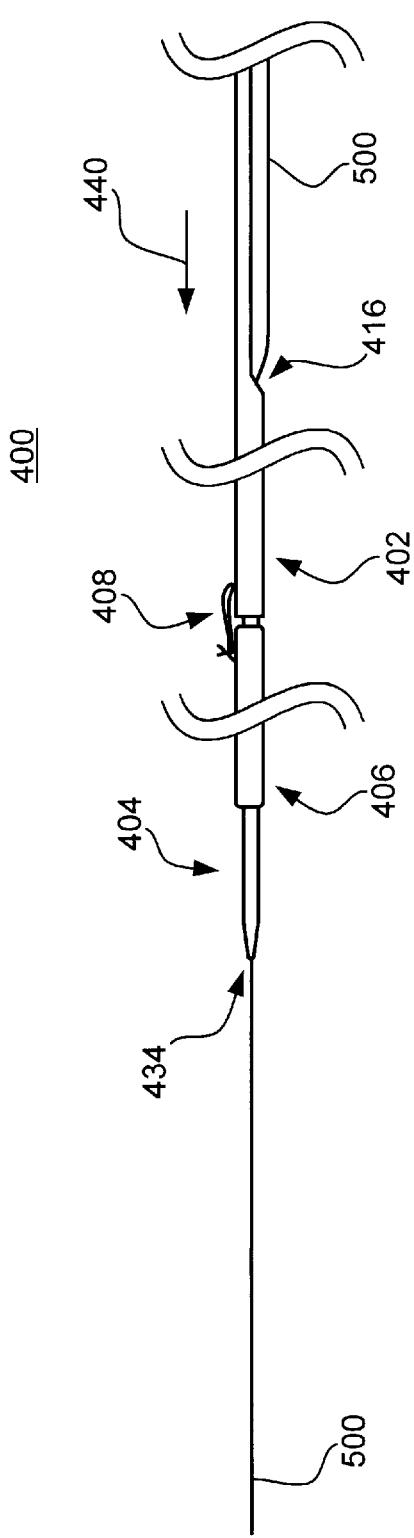
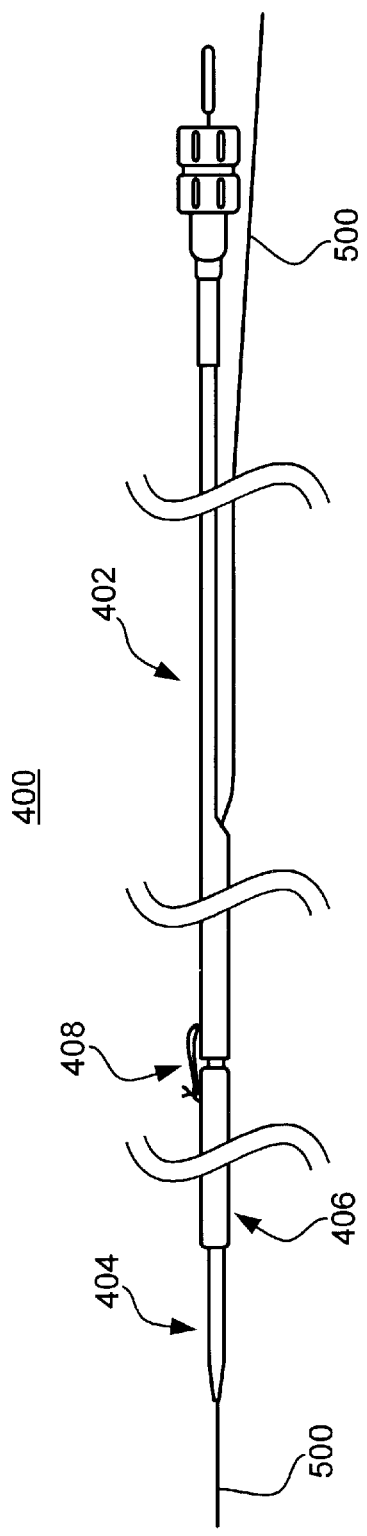

DRAINAGE CATHETER DELIVERY SYSTEM

CROSS-REFERENCE TO CO-PENDING APPLICATION

This application is a continuation of co-pending U.S. patent application Ser. No. 09/312,341, filed May 14, 1999, now U.S. Pat. No. 6,248,100 which is a continuation-in-part of co-pending patent application Ser. No. 09/257,764, filed on Feb. 25, 1999, now U.S. Pat. No. 6,264,624 which is a continuation of patent application Ser. No. 08/911,323 filed on Aug. 14, 1997, now issued U.S. Pat. No. 5,921,952, the entire disclosures of which are hereby incorporated by reference.

FIELD OF THE INVENTION

The present invention generally relates to drainage catheters. More specifically, the present invention relates to a system and method for delivering a drainage catheter within a body cavity.

BACKGROUND OF THE INVENTION

A drainage catheter or stent is widely recognized as an efficient and effective device for treating an obstructed body cavity, such as the ducts of the biliary tree or a ureter. These stents are used to bypass and drain an obstructed lumen and can be configured for long-term positioning within the lumen. It should be understood that the terms "drainage catheter" and "stent" can be used interchangeably with reference to these applications.

While drainage catheters are highly useful, proper placement of the drainage catheter often is a difficult and time-consuming procedure. Typically, an endoscope is first placed into the body cavity and positioned at the proper anatomical area. In this regard, a distal end of the endoscope is placed in close proximity to the desired area of drainage catheter placement. If necessary, a pre-dilating device is directed through the distal end of the endoscope to dilate the stricture. The dilating device is removed from the endoscope and replaced by a guidewire. Then, a guide catheter is placed over the guidewire and positioned near the stricture. The drainage catheter or stent is placed over the guide catheter until a proximal end of the drainage catheter is beyond a proximal end of the guide catheter. A push catheter is then placed over the guide catheter until a distal end of the push catheter abuts the proximal end of the drainage catheter. The drainage catheter is then pushed via the push catheter down the length of the guide catheter until the drainage catheter reaches the desired body cavity location. At this point, the drainage catheter is manipulated via the push catheter to secure the drainage catheter within the stricture.

Once properly positioned, the guide catheter and guidewire are removed from inside of the push catheter and the drainage catheter. The push catheter remains in place to prevent movement of the drainage catheter during removal of the guide catheter and guidewire.

Every effort is made to secure the drainage catheter at the proper location within the body cavity. However, there are times when the drainage catheter is placed too far into the body or migrates to a less desirable location in which case there are several time-consuming secondary procedures available to correctly position the drainage catheter. These may include placing the endoscope back into the body and directing a tool into the endoscope to grasp the drainage catheter and pull it back into position. However, it is not possible to retract the drainage catheter with the push catheter because retraction of the push catheter simply pulls the push catheter away from the drainage catheter.

In addition to the difficulties associated with drainage catheter repositioning, there are also difficulties associated with guidewire positioning. Specifically, it is sometimes difficult to maintain the position of the guidewire in the patient while the delivery system is advanced along the guidewire. Typically, two people are required to deliver a drainage catheter, one person to hold the scope handle and feed the delivery system, another person to hold the hub of the delivery system and pull on the guidewire as the delivery system is advanced. If these two operations are not synchronized, the guidewire position inside the patient may be compromised.

Drainage catheters are highly beneficial devices from a clinical stand point. However, the procedures involved in positioning or re-positioning a drainage catheter are very time-consuming and leave little room for error. Therefore, a substantial need exists for an improved drainage catheter delivery system to address these shortcomings.

SUMMARY OF THE INVENTION

The present invention provides a delivery system for deploying a drainage catheter within a body cavity. The delivery system is designed for use with a conventional guidewire and generally includes a placement catheter (a.k.a. push catheter), a drainage catheter (a.k.a. stent), a guide member (a.k.a. guide catheter or wire guide), and a retention device. The delivery system allows single operator, one-step placement and simple repositioning of the drainage catheter. The delivery system also allows the treating physician to place a drainage catheter without compromising guidewire position and to reposition the drainage catheter without using additional tools.

An exemplary embodiment of the present invention provides a drainage catheter delivery system including a guide member having a guidewire lumen extending from a proximal guidewire port located distal of the proximal end of the guide member. A placement catheter is disposed over the guide member and is longitudinally movable relative thereto. Preferably, the placement catheter has a catheter lumen extending from a proximal guidewire port located distal of the proximal end of the placement catheter. Locating the proximal guidewire ports as such allows the delivery system to be used by a single operator with a shorter, easier-to-handle guidewire.

A drainage catheter is disposed about the guide member distal of the placement catheter. The drainage catheter delivery system preferably includes a means for releasably connecting the placement catheter to the drainage catheter, wherein the releasable connecting means disconnects the drainage catheter upon displacement of the guide member. The releasable connecting means may comprise a tying mechanism such as a flexible thread or suture. The flexible thread passes through a passage in the drainage catheter and a passage in the placement catheter, and forms a loop around the distal portion of the guide member disposed in the drainage catheter.

A proximal portion of the guide member may include a stop mechanism which limits proximal displacement of the guide member relative to the placement catheter. The distal portion of the guide member may comprise a tube, and the proximal portion may comprise a low profile wire. Both the proximal and distal portions of the placement catheter may comprise tubes, wherein the distal tubular portion of the guide member is disposed in the distal tubular portion of the placement catheter, and the proximal wire portion of the guide member is disposed in the proximal tubular portion of the placement catheter. Preferably, the distal portion of the placement catheter is longer than the distal portion of the guide member, and the proximal portion of the placement catheter is shorter than the proximal portion of the guide member.

The present invention also provides a method of delivering a drainage catheter to a target site in a duct of a patient. The method involves the steps of inserting a guidewire into the duct, partially advancing the delivery system over the guidewire until the guidewire exits the proximal guidewire port of the delivery system, holding the exit portion of the guidewire, and further advancing the delivery system over the guidewire until the drainage catheter is adjacent the target site in the duct.

BRIEF DESCRIPTION OF THE DRAWINGS

FIG. 1 is a side view of a delivery system in accordance with an embodiment of the prevent invention;

FIG. 2 is an enlarged side view of a guide catheter portion of the delivery system in accordance with the present invention;

FIG. 3 is an enlarged side view of a push catheter portion of the delivery system in accordance with the present invention;

FIG. 4 is a side view of the assembled delivery system in accordance with the present invention;

FIGS. 5–10 illustrate steps of assembling the delivery system in accordance with the present invention;

FIG. 14 is a side cross-sectional view of a delivery system in accordance with another embodiment of the present invention;

FIG. 14A is an enlarged side cross-sectional view of a portion of the delivery system of FIG. 14 in accordance with the present invention;

FIGS. 19–21 illustrate use of the delivery system of FIG. 18, including release of the stent;

FIG. 22A is an enlarged, cross-sectional view of the delivery system in accordance with the present invention positioned within an endoscope;

FIG. 22B is an enlarged, cross-sectional view of the delivery system in accordance with the present invention disposed within an endoscope;

FIG. 23 is a perspective view of a sheath used in conjunction with an alternative embodiment of a delivery system in accordance with the present invention;

FIG. 23A is an enlarged perspective view of a portion of the sheath of FIG. 22;

FIG. 23B is an enlarged perspective view of a portion of a sheath in accordance with an alternative embodiment of the present invention;

FIG. 24 is a side view of a drainage catheter delivery system in accordance with yet another embodiment of the present invention;

FIG. 25 is a side view of a placement catheter for use in the delivery system illustrated in FIG. 24;

FIG. 26 is a side view of a guide member for use in the delivery system illustrated in FIG. 24;

FIG. 27 is a cross-sectional view taken along line 27—27 in FIG. 26;

FIG. 28 is a cross-sectional view taken along line 28—28 in FIG. 25;

FIG. 29 is a cross-sectional view taken along line 29—29 in FIG. 25;

FIG. 30 is a cross-sectional view taken along line 30—30 in FIG. 26;

FIG. 31 is a side view of the delivery system illustrated in FIG. 24, disposed on a guidewire;

FIG. 32 is a cross-sectional view taken along line 32—32 in FIG. 31;

FIG. 33 is a cross-sectional view taken along line 33—33 in FIG. 31;

FIG. 34 is a cross-sectional view taken along line 34—34 in FIG. 31;

FIG. 35 is a cross-sectional view taken along line 35—35 in FIG. 31;

FIG. 36 is a cross-sectional view taken along line 36—36 in FIG. 31; and

FIGS. 37A–37D are side views illustrating a method of use of the delivery system illustrated in FIG. 24.

DETAILED DESCRIPTION OF THE INVENTION

Figure 10:
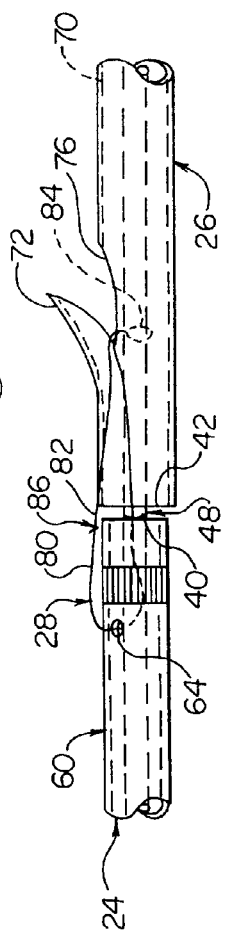

The following detailed description should be read with reference to the drawings in which similar elements in different drawings are numbered the same. The drawings, which are not necessarily to scale, depict illustrative embodiments and are not intended to limit the scope of the invention.

A preferred embodiment of a delivery system 20 is shown in FIG. 1. The delivery system 20 includes a guide catheter 22, a push catheter 24, a stent 26 and a retention device 28. Although described herein as a preferred device and method for delivering a stent or drainage catheter, the medical device deployment system could be utilized to deliver other units.

The various components of the delivery system 20 are described in greater detail below. Generally, however, the guide catheter 22 includes a proximal end 30, an intermediate portion 32 and a distal end 34. The push catheter 24 includes a proximal end 38 and a distal end 40. Similarly, the stent 26 includes a proximal end 42 and a distal end 44. The intermediate portion 32 of the guide catheter 22 is sized to slidably receive the push catheter 24 and the stent 26. Finally, the retention device 28 is configured to selectively secure the stent 26 to the push catheter 24. In this regard, the distal end 40 of the push catheter 24 is sized to abut the proximal end 42 of the stent 26. Thus, upon final assembly, distal movement of the push catheter 24 relative to the guide catheter 22 imparts a distal motion onto the stent 26 via interaction of the distal end 40 of the guide catheter 22 with the proximal end 42 of the stent 26. Conversely, proximal movement of the push catheter 24 relative to the guide catheter 22 imparts a similar proximal (or retraction) movement onto the stent 26 via the retention device 28.

The guide catheter 22 is shown in greater detail in FIG. 2. The guide catheter 22 includes a guide catheter body 48 defined by the proximal end 30, the intermediate portion 32 and the distal end 34, a male luer connector 50, radiopaque markings 52*a–c* and a central lumen (not shown). The male luer connector 50 is of a type commonly known in the art and is preferably positioned at the proximal end 30 of the guide catheter body 48. The radiopaque markings 52*a–c* are formed along the intermediate portion 32 at predetermined locations to assist in fluoroscopically determining system positioning. The guide catheter 22 is preferably formed from a relatively stiff biocompatible polymer via an extrusion process. Alternatively, a biocompatible metal may be used. The central lumen (not shown) is preferably formed to extend from the proximal end 30 to the distal end 34. In the preferred embodiment, the central lumen is appropriately sized to slidably receive a guidewire and is preferably 0.038 inches in diameter. It should be recognized that other diameters are equally acceptable. With this configuration, the male luer connector includes a transverse passage (not shown) in communication with the central lumen for receiving a guidewire. Finally, the distal end 34 of the guide catheter body 48 is preferably formed to include a tapered tip 54. As described in greater detail below, the tapered tip 54 assists in dilation of a body cavity stricture. In a preferred embodiment, the tapered tip is coated with a lubricant to facilitate movement of the guide catheter body 48 within a body cavity.

The push catheter 24 is shown in greater detail in FIG. 3. The push catheter 24 includes a female luer lock connector 58 and a push catheter body 60. The push catheter body 60 is defined by the proximal end 38 and the distal end 40, and includes a central lumen 62, an opening 64 and a radiopaque marking 66.

The female luer lock connector 58 is of a type commonly known in the art and is attached to the proximal end 38 of the push catheter body 60. In a preferred embodiment, the female luer lock connector 58 includes a transverse opening (not shown) in communication with the central lumen 62.

The central lumen 62 of the push catheter body 60 extends from the proximal end 38 to the distal end 40. As described in greater detail below, the central lumen 62 has a diameter greater than an outer diameter of the guide catheter body 48 (FIG. 2). The opening 64 is positioned near the distal end 40 of the push catheter body 60, passing from an outer circumference of the push catheter body 60 to the central lumen 62. Finally, the radiopaque marking 66 is positioned near the distal end 40 of the push catheter body 60 to facilitate fluoroscopic positioning of the push catheter 24. The push catheter body 60 is preferably formed of a relatively rigid biocompatible polymer through an extrusion process. Alternatively, a biocompatible metal may be used. The push catheter body 60 has a length less than the length of the guide catheter body 48. Following extrusion of the push catheter body 60, the female luer lock connector 58 is attached to the proximal end 38.

The stent 26, in conjunction with the delivery system 20, is shown in greater detail in FIG. 4. The stent 26 includes the proximal end 42, the distal end 44, a central lumen 70, a proximal barb 72 and a distal barb 74. The central lumen 70 extends from the proximal end 42 to the distal end 44. The proximal barb 72 extends outwardly in a distal fashion from an outer circumference of the stent 26. In a preferred embodiment, the proximal barb 72 creates a passage 76 (shown partially in FIG. 4) extending from an outer circumference of the stent 26 to the central lumen 70. Similarly, the distal barb 74 extends from an outer circumference of the stent 26 in a proximal fashion. The proximal barb 72 and the distal barb 74 assist in maintaining position of the stent 26 within a body cavity. The barbs are opposed to one another to prevent stent migration in either axial direction.

The central lumen 70 of the stent 26 is sized to slidably engage the guide catheter 22. In this regard, the central lumen 70 has a diameter greater than an outer diameter of the guide catheter body 48. Further, the stent 26 has a length less than a length of the guide catheter body 48. Thus, upon final assembly, the push catheter 24 and the stent 26 have a combined length less than that of the guide catheter body 48. The stent 26 is preferably formed from a biocompatible, relatively flexible material, such as plastic. Alternatively, a biocompatible metal may be used. In one preferred embodiment, the stent 26 is coated with a hydrophilic lubricant on the outer circumference to facilitate movement of the stent 26 within a body cavity. Additionally, the lubricious coating assists in reducing the potential for encrustation within the body cavity. In this regard, the central lumen 70 may also be coated with a hydrophilic material to facilitate movement of the stent 26 along the guide catheter body 48, as well as limit encrustation of the stent 26. Finally, the proximal barb 72 and the distal barb 74 are preferably formed in the stent 26 by imparting properly positioned cuts through the stent wall. Other agents, such as antimicrobial agents, may be incorporated into the stent coating or polymer.

While the delivery system 20 of the present invention has been described as preferably including the stent 26, other components may be used. More particularly, the stent 26 maybe a drainage catheter or similar device. Similar to the stent 26 shown in FIG. 4, the drainage catheter (not shown) includes a central lumen sized to slidably engage an outer circumference of the guide catheter body 48. Further, the drainage catheter is preferably configured to include a passage similar to the passage 76 of the stent 26 shown in FIG. 4 for receiving the retention device 28. Thus, for purposes of this description, the term "stent" is interchangeable with the term "drainage catheter", as will be understood by one skilled in the art.

As shown in FIG. 4, the retention device 28 is preferably a flexible thread. In one preferred embodiment, the retention device 28 is a biocompatible suture. The suture can be a thread, filament or wire. Alternatively, the retention device 28 can be a biocompatible wire or cable. Regardless, the suture 26 preferably extends from the proximal end 38 of the push catheter 24. As described in greater detail below, the suture 26 connects the push catheter 24 to the stent 26 via the opening 64 in the push catheter 24 and the passage 76 in the stent 26.

As shown in FIG. 4, the delivery system 20 is assembled prior to insertion into the body either by the manufacturer or by the physician by sliding the push catheter 24 over the guide catheter body 48. As previously described, the push catheter 24 includes a central lumen 62 having a diameter greater than that of the guide catheter body 48. The proximal end 38 of the push catheter 24 is maneuvered toward the proximal end 30 of the guide catheter body 48 until the distal end 34 of the guide catheter body 48 extends slightly from the distal end 40 of the push catheter 24. The proximal end 42 of the stent 26 is then positioned about the distal end 34 of the guide catheter body 48. The retention device 28 is used to secure the push catheter 24 to the stent 26.

More particularly, as shown in FIG. 5, the distal end 40 of the push catheter body 60 includes the opening 64. As previously described, the opening 64 passes from the central lumen 62 to an outer circumference of the push catheter body 60.

As shown in FIG. 6, the retention device 28, which in the preferred embodiment is a flexible thread or suture, is threaded through the opening 64 in the push catheter body 60. In this regard, the suture 28 includes a first end 80 and a second end 82. The suture 28 is positioned through the opening 64 such that the first end 80 extends away from an outer circumference of the push catheter body 60. Conversely, the second end 82 of the suture 28 extends within the central lumen 62 of the push catheter body 60.

As shown in FIG. 7, the guide catheter body 48 is slidably directed within the central lumen 62 of the push catheter body 60 until the distal end 40 of the push catheter body 60 is proximal the distal end 34 of the guide catheter body 48. The stent 26 is axially placed over the guide catheter body 48. As shown in FIG. 7, when the stent 26 is first placed over the guide catheter body 48, the distal end 34 of the guide catheter body 48 is initially directed through the central lumen 70 of the stent 26 at the proximal end 42. Subsequently, the distal end 34 of the guide catheter body 48 is directed outwardly from the central lumen 70 of the stent 26 via the passage 76 created by the proximal barb 72. Once so positioned, the stent 26 is slid over the guide catheter body 48 to a position in close proximity to the distal end 34 of the push catheter body 60. Notably, the second end 82 of the suture 28 is maneuvered away from the central lumen 62 of the push catheter body 60, above an outer circumference of the stent 26.

As shown in FIG. 8, the second end 82 of the suture 28 is looped around the guide catheter body 48, distal the proximal barb 72 of the stent 26. Thus, in the position shown in FIG. 8, the suture 28 forms a loop 84 about the guide catheter body 48. The loop 84 is maneuvered toward the proximal barb 72 of the stent 26 by pulling the second end 82 of the suture 28 toward the distal end 40 of the push catheter body 60. With the loop 84 positioned near the proximal barb 72 of the stent 26, the guide catheter body 48 is retracted relative to the stent 26. More particularly, the distal end 34 of the guide catheter body 48 is slowly directed into the passage 76 of the stent 26. During this retraction movement, the loop 84 of the suture 28 remains engaged with the guide catheter body 48. Once the tapered tip 54 of the guide catheter body 48 clears the passage 76 of the stent 26, the distal end 34 of the guide catheter body 48 is re-inserted into the central lumen 70 of the stent 26.

As shown in FIG. 9, the distal end 34 of the guide catheter body 48 is now entirely within the central lumen 70 of the stent 26. Further, the loop 84 of the suture 28 passes through the passage 76 of the stent 26 and remains engaged with the guide catheter body 48. The distal end 34 of the guide catheter body 48 is then slid forward relative to the stent 26 so that the loop 84 of the suture 28 remains in contact with the guide catheter body 48. It is recognized that in an alternative embodiment, a separate hole could be made in the stent wall for passing the suture through, rather than using the passage 76 that is created by forming the barb.

Finally, as shown in FIG. 10, the first end 80 and the second end 82 of the suture 28 are secured to one another, forming a knot 86. Thus, upon final assembly, the suture or retention device 28 connects the push catheter 24 to the stent 26 so long as the loop 84 is engaged with the guide catheter body 48.

During use, the delivery system 20 is pre-assembled as previously described. In a preferred embodiment, an endoscope is positioned within a body cavity so that a distal end of the endoscope is located near a stricture to be stented or other desired location.

The distal end 34 of the guide catheter 22 preferably extends outwardly from the distal end 44 of the stent 26 (shown in FIG. 4). As previously described, the distal end 34 of the guide catheter 22 includes the tapered tip 54. As the guide catheter body 48 exits the distal end of the endoscope, the tapered tip 54 dilates the stricture. It is recognized that this placement can be accomplished over a guidewire which has been previously placed across a stricture with the guide catheter including a lumen which threads over the guidewire.

Once the distal end 34 of the guide catheter body 48 is properly positioned, the stent 26 is then positioned within the body cavity. More particularly, the guide catheter 22 is held in a stationary position. The push catheter 24 is then moved forward (to the right in FIG. 10) such that the distal end 40 of the push catheter 24 contacts the proximal end 42 of the stent 26. Continued forward movement of the push catheter 24 imparts a similar movement onto the stent 26. If retraction (leftward movement with reference to FIG. 10) of the stent 26 is required, the guide catheter body 48 is again held stationary. The push catheter 24, in turn, is retracted. Retraction of the push catheter 24 creates a leftward movement on the suture 28 via the opening 64. Because the suture 28 is secured to the guide catheter 22 via the loop 84, retraction of the push catheter 24 will cause the suture 28 to become relatively taut. At this point, the suture 28 imparts a leftward or retraction movement onto the stent 26 via contact between the suture and the stent 26 at the passage 76. Notably, the loop 84 will slide along the guide catheter body 48 such that once the suture 28 is taut, retraction of the push catheter 24 results in retraction of the stent 26.

Figure 11:
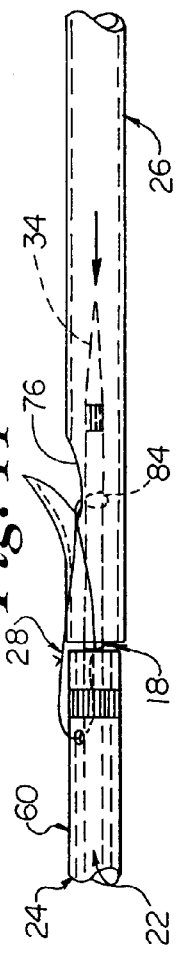
FIGS. 11–13 illustrate use of the delivery system of the present invention, including release of the retention device.

Once the stent 26 is positioned within the body cavity at a desired location, the guide catheter 22, the push catheter 24 and the retention device or suture 28 are removed. More particularly, as shown in FIG. 11, the suture 28 is disengaged from the stent 26 by first retracting the guide catheter body 48 while the push catheter 24 is held stationary. As previously described, the loop 84 slides along the guide catheter body 48. Retraction of the guide catheter 22 continues until the distal end 34 clears the loop 84. In other words, the loop 84 continues to slide along the guide catheter body 48 as the guide catheter 22 is retracted. Once the distal end 34 of the guide catheter body 48 is approximately equal with the passage 76 in the stent 26, the loop 84 will slide off of, or out of engagement with, the guide catheter body 48.

Figure 12:
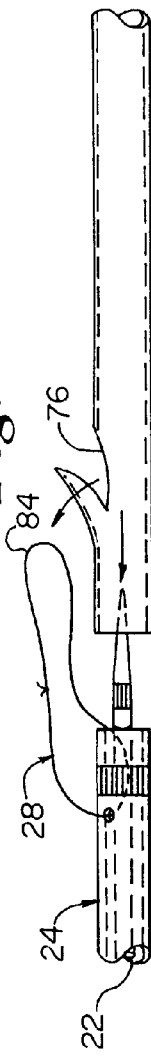
Figure 13:
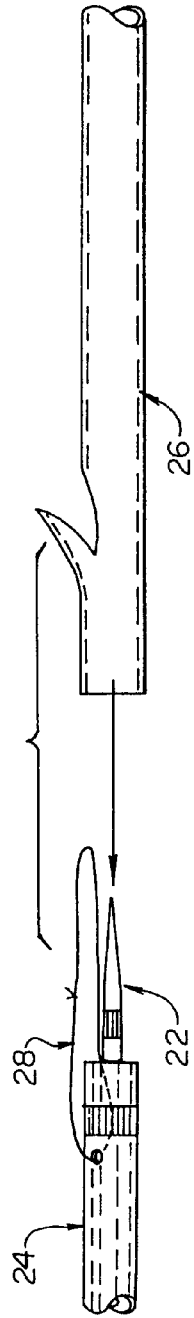

As shown in FIG. 12, once the loop 84 is free from the guide catheter body 48, the guide catheter 22 and the push catheter 24 can be retracted from the body cavity. Retraction (or leftward movement in FIG. 12) of the push catheter 24 pulls the suture 28 out of the passage 76 and away from the stent 26. Finally, as shown in FIG. 13, the guide catheter 22, the push catheter 24 and the suture 28 are completely removed from the body cavity, leaving the stent 26 permanently positioned within the body cavity.

The delivery system of the present invention presents a unique, single-step approach for delivering a drainage catheter or stent drainage catheter. Unlike prior procedures which require numerous components and time-consuming steps for correcting minor misplacement of the drainage catheter or stent, the delivery system of the prevent invention is a single, pre-assembled tool which provides for both forward and rearward movement of the drainage catheter or stent within the body cavity. Further, in one preferred embodiment, incorporation of various radiopaque markings in conjunction with lubricious coating on the drainage catheter or stent facilitates proper device placement.

In another alternative embodiment, the suture 28 could be permanently attached to the stent and temporarily to the push catheter through a loop extending through a hole in the push catheter. Essentially the ends of the suture would be reversed from the previous embodiments. The suture could be used to facilitate stent removal if left in place on the stent.

An alternative delivery system 100 is shown in FIG. 14. The delivery system 100 includes a placement or push catheter 102, guide member 104 (a.k.a. wire guide or guide catheter), a stent or drainage catheter 106, and a retention device 108. The various components of the delivery system 100 are described in greater detail below. Generally, however, the placement catheter 102 includes a proximal portion 110, an intermediate portion 112 and a distal portion 114. The placement catheter further defines a central lumen 116. The guide member 104 includes a proximal end 118 and a distal end 120. Similarly, the stent 106 includes a proximal end 122 and a distal end 124. The placement catheter lumen 116 is sized to slidably receive the guide member 104. Further, the distal portion 114 of the placement catheter is sized to coaxially receive the drainage catheter 106. Finally, the retention device 108 is configured to selectively secure the stent 106 to the placement catheter 102. Thus, upon final assembly, distal movement (or advancement) of the placement catheter 102 imparts a distal motion onto the drainage catheter 106 via interaction with the proximal end 122 of the stent 106. Conversely, proximal movement (or retraction) of the placement catheter 102 imparts a similar proximal (or retraction) movement onto the drainage catheter 106 via the retention device 108.

The placement catheter 102 includes a placement catheter body 126, defining the proximal portion 110, the intermediate surface 112, the distal portion 114 and the placement catheter lumen 116, and a placement catheter hub 128. The placement catheter hub 128 is of a type commonly known in the art and is preferably positioned at the proximal portion 110 of the placement catheter body 126.

The intermediate portion 112 preferably has a larger outer diameter than the distal portion 114. In this regard, an abutment surface 130 is formed at a distal end of the intermediate portion 112. The intermediate potion 130 further includes an opening 132 for securing a portion of the retention device 108. The opening 132 extends from an outer circumference to the placement catheter lumen 116, and is preferably located proximal the abutment surface 130.

The distal portion 114 of the placement catheter body 126 is preferably formed to include a hole 134 and a tapered tip 136. The distal portion 114 preferably has a length greater than a length of the stent 106, for reasons explained below. The hole 134 extends from an outer circumference to the placement catheter lumen 116, and is sized to allow passage of a portion of the retention device 108. The hole 134 is preferably positioned distal the abutment surface 130. As described in greater detail below, the tapered tip 136 assists in dilation of a body cavity stricture.

In a preferred embodiment, the placement catheter 102 is constructed to include a rapid exchange feature. In particular, a channel 138 extends longitudinally along the proximal portion 110 and the intermediate portion 112 of the placement catheter body 126. The channel 138 extends from an outer circumference of the placement catheter body 126 to the placement catheter lumen 116, and terminates at a proximal end 140 and a distal end 142. The channel 138 is sized to have a diameter greater than a diameter of a guidewire (not shown) disposed within the placement catheter lumen 116. With this configuration, the channel 138 allows movement of the guidewire into and out of the placement catheter lumen 116.

The placement catheter 102 is preferably formed from a relatively stiff biocompatible polymer via an extrusion process. Alternatively, a biocompatible metal may be used. The placement catheter lumen 116 is preferably formed to extend from the proximal portion 110 to the distal portion 114. The opening 132, the hole 134 and the channel 138 can be formed by known manufacturing techniques, such as imparting necessary cuts into the placement catheter body 126 following extrusion.

The guide member 104 includes a guide member body 144 and a guide member hub 146. The guide member body 144 is defined by the proximal end 118 and the distal end 120. The guide member hub 146 is of a type commonly known in the art and is attached to the proximal end 118 of the guide member body 144.

As previously described, the guide member body 144 has an outer diameter less than a diameter of the placement catheter lumen 116. The distal end 120 of the guide member body 144 is preferably configured to receive a guidewire (not shown). In this regard, the distal end 120 preferably forms a pocket 148. As described in greater detail below, the pocket 148 is preferably tapered.

The guide member body 144 has a length greater than the intermediate portion 112 of the placement catheter 102. For example, in the loading position shown in FIG. 14, the guide member hub 146 approximately abuts a proximal side of the placement catheter hub 128, whereas the guide member body 144 extends within the placement catheter lumen 116. More particularly, the guide member body 144 has a length such that the distal end 120 of the guide member body 144 extends to a point distal the abutment surface 130 of the placement catheter body 126 in the loading position.

Figure 15:
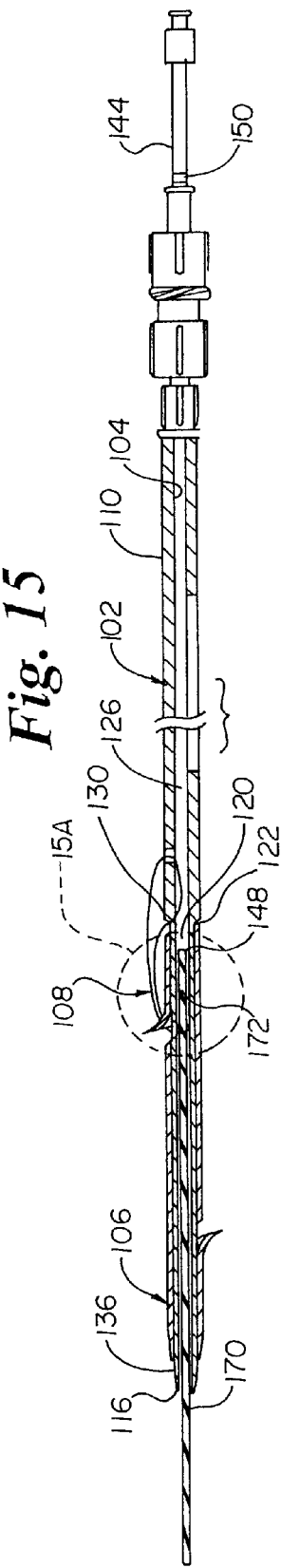
FIG. 15 is a side cross-sectional view of the delivery system of FIG. 14, depicting the delivery system advanced over a guidewire in accordance with the present invention.

Finally, the guide member body 144 preferably includes a safety marking 150 (shown in FIG. 15). As described in greater detail below, the safety marking 150 is positioned along the guide member body 144 distal the proximal end 118 to provide visual indication of positioning of the guide member body 144 within the placement catheter 102.

The guide member body 144 is preferably formed of a relatively rigid biocompatible polymer through an extrusion process. Alternatively, a biocompatible metal may be used. The guide member body 144 may be solid, or may include a central lumen. Regardless of exact form, the distal end 120 of the guide member body 144 is shaped to form the pocket 148 following extrusion.

Although the guide member 104 has been preferably described as an elongated body extending through the placement catheter, other configurations of the guide member are also acceptable. For example, the-guide member may be a relatively small component extending from a portion of the placement catheter, sized to guide movement of the guidewire relative to the drainage catheter. In this regard, a portion of the guide member must be sized to extend within the drainage catheter lumen to guide the guidewire into engagement with the retention device.

The drainage catheter 106 includes the proximal end 122, the distal end 124, a drainage catheter lumen 152, a proximal barb 154 and a distal barb 156. The drainage catheter lumen 152 extends from the proximal end 122 to the distal end 124. The proximal barb 154 extends outwardly in a distal fashion from an outer circumference of the drainage catheter 106. In a preferred embodiment, the proximal barb 154 creates a passage 158 extending from an outer circumference of the drainage catheter 106 to the drainage catheter lumen 152. Similarly, the distal barb 156 extends from an outer circumference of the drainage catheter 106 in a proximal fashion. The proximal barb 154 and the distal barb 156 assist in maintaining position of the drainage catheter 106 within a body cavity. The barbs 154, 156 are opposed to one another to prevent drainage catheter migration in either axial direction following implant.

The drainage catheter lumen 152 is sized to slidably engage the distal portion 114 of the placement catheter body 126. In this regard, the drainage catheter lumen 152 has a diameter greater than an outer diameter of the distal portion 114 of the placement catheter body 126. Importantly, the drainage catheter lumen 152 has a diameter less than a diameter of the intermediate portion 112, and in particular the abutment surface 130, of the placement catheter body 126. Finally, the drainage catheter 106 has a length less than a length of the distal portion 114 of the placement catheter 102. Thus, upon final assembly, the tapered tip 136 of the placement catheter body 126 extends from the distal end 124 of the drainage catheter 106.

The drainage catheter 106 is preferably formed from a biocompatible, relatively flexible material, such as plastic. Alternatively, a biocompatible metal may be used. The proximal barb 154 and the distal barb 156 are preferably formed in the drainage catheter 106 by imparting properly positioned cuts through the drainage catheter 106 wall.

The retention device 108 is preferably a flexible thread. In one preferred embodiment, the retention device 108 is a biocompatible suture. The suture can be a thread, filament or a wire. Alternatively, the retention device 108 can be a biocompatible wire or cable. Regardless of exact form, the retention device 108 preferably extends from the placement catheter body 126 from a point proximal the abutment surface 130. As described in greater detail below, the retention device 108 connects the placement catheter 102 to the drainage catheter 106 via the hole 134 in the placement catheter body 126 and the passage 158 in the drainage catheter 106.

The delivery system 100 is assembled prior to insertion in the body either by the manufacturer or by a physician. The retention device 108 is first secured to the placement catheter 102. The retention device 108 is preferably a flexible thread, shown in FIG. 14 as forming a continuous loop. Prior to assembly, however, the flexible thread 108 is defined by opposing ends which are subsequently attached at a knot 162 to form the continuous loop. Before forming the knot 102, then, one of the opposing ends is fed through the opening 132 in the placement catheter body 126 and directed distally within the placement catheter lumen 116. The placement catheter body 126 preferably includes an additional opening (not shown) to facilitate passage of the end of the flexible thread 108 from the placement catheter lumen 116. The ends of the flexible thread 108 can then be joined by the knot 162 to form a continuous loop. Alternatively, the ends of the flexible thread 108 can remain unattached until subsequent assembly steps have been performed.

While the retention device 108 has been preferably described as a flexible thread passing through two openings in the placement catheter body 126, other forms of attachment are acceptable. The retention device may be a flexible thread permanently or releasably secured to the placement catheter. For example, the retention device 108 may be secured during extrusion of the placement catheter body 126 such that the placement catheter body 126 is molded around or otherwise encompasses a portion of the retention device 108. Alternatively, the retention device can be an interlocking device positioned at the distal end of the placement catheter, configured to be releasably attached to the proximal end of the drainage catheter. With this later configuration, the placement catheter can engage and disengage the stent or drainage catheter by simple rotational movement of the placement catheter relative to the drainage catheter.

The drainage catheter 106 is then slid over the distal portion 114 of the placement catheter 102. As previously described, the drainage catheter lumen 152 has a diameter greater than that of the distal portion 114 of the placement catheter body 126. The drainage catheter 106 is maneuvered along the distal portion 114 of the placement catheter 102 until the proximal end 122 of the drainage catheter 106 approximately abuts the abutment surface 130 of the placement catheter 102. In this position, the passage 158 of the drainage catheter 106 and the hole 134 in the distal portion 114 of the placement catheter body 126 are appropriately aligned.

The guide member 104 is positioned within the placement catheter lumen 116. More particularly, the distal end 120 of the guide member body 144 is placed within the placement catheter lumen 116 at the proximal portion 110 of the placement catheter body 126. The guide member 104 is then advanced within the placement catheter lumen 116, maneuvering the distal end 120 of the guide member 104 toward the abutment surface 130 of the placement catheter 102. The retention device 108 is then used to secure the placement catheter 102 to the drainage catheter 106.

With the retention device 108 properly secured to the placement catheter 102, a leading portion 164 of the retention device 108 is extended distally toward the drainage catheter 106. More particularly, the leading portion 164 of the retention device 108 is advanced through the passage 158 in the drainage catheter 106 and through the hole 134 of the distal portion 114 of the placement catheter body 126. This orientation is best shown in FIG. 14A whereby the leading portion 164 of the retention device 108 is extended into the placement catheter lumen 116. With a preferred assembly approach, the leading portion 164 of the retention device 108 is formed as a loop end, approximately nesting against the wall of the placement catheter lumen 116. The guide member 104 is then slid in a distal fashion through the placement catheter lumen 116 such that the distal end 120 of the guide member body 144 engages the leading portion 164 of the retention device 108. Notably, as shown in FIG. 14, the distal end 120 of the guide member body 126 includes a slight taper such that the distal end 120 will easily slide over the leading portion 164 of the retention device 108.

In an alternative embodiment, the knot 164 in the retention device 108 is not formed prior to guide member 104 engagement. With this approach, the guide member 104 can be advanced to the position shown in FIG. 14, and a leading end of the retention device 108 threaded around the guide member body 126. The leading end of the retention device 108 is directed away from the drainage catheter 106 and secured with the knot 162.

The guide member 104 is advanced within the placement catheter lumen 116 until the guide member hub 146 contacts the placement catheter hub 128, as shown in FIG. 14. The guide member hub 146 is secured to the placement catheter hub 128, such that the delivery system is "locked" in the loading position depicted in FIG. 14. Upon final assembly, then, the retention device 108 connects the placement catheter 102 to the drainage catheter 106 so long as the retention device 108 engages the guide member 104.

During use, the delivery system 100 is pre-assembled as previously described. In a preferred embodiment, an endoscope is positioned within a body cavity so that a distal end of the endoscope is located near a stricture to be stented or other desired location. Further, a guidewire is directed through the endoscope. The guidewire position is maintained within the endoscope elevator such that a proximal end of the guidewire is accessible from a proximal end of the endoscope.

The guide member hub 146 is unlocked from the placement catheter hub 128 and the delivery system 100 advanced over the guidewire 170 to a transfer position shown in FIG. 15. In this regard, the proximal end 172 of the guidewire 170 first enters the placement catheter lumen 116 at the tapered tip 136. The delivery system 100 is further advanced over the guidewire 170 such that the proximal end 172 of the guidewire 170 engages the distal end 120 of the guide member body 126. As previously described, the distal end 120 of the guide member body 126 forms a pocket 148 which is sized to receive the proximal end 172 of the guidewire 170.

The placement catheter 102 is further advanced over the guidewire 170 after initial engagement with the guidewire 170. The drainage catheter 106 is likewise advanced, via interaction of the abutment surface 130 of the placement catheter 102 with the proximal end 122 of the drainage catheter 106. The guide member 104, however, will no longer advance. Advancement or distal movement of the placement catheter 102 results in the proximal end 172 of the guidewire 170 moving toward the proximal portion 110 of the placement catheter 102. This movement, in turn, forces the guide member 104 to retract from the placement catheter 102 as shown in FIG. 15.

Figure 15A:
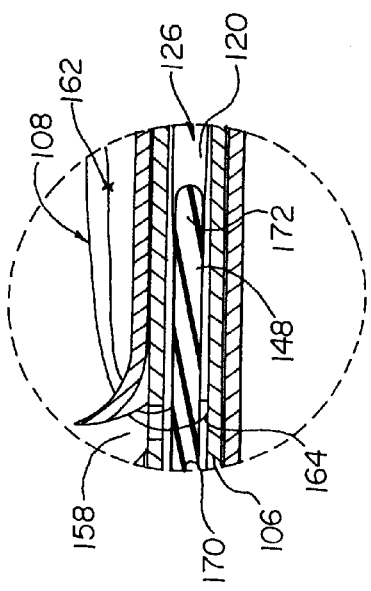
FIG. 15A is an enlarged, side cross-sectional view of a portion of the delivery system of FIG. 15 in accordance with the present invention.

As the proximal end 172 of the guidewire 170 moves toward the abutment surface 130 of the placement catheter 102, engagement of the retention device 108 with the guide member body 126 is transferred to the guidewire 170. As shown in FIG. 15A, the distal end 120 of the guide member body 126 is slightly tapered so as to present a relatively smooth surface to the leading portion 164 of the retention device 108. As the placement catheter 102 is advanced over the guidewire 170, the leading portion 164 of the retention device 108 slides along the guide member body 126 and then to the guidewire 170.

Once the placement catheter 102 has been advanced along the guidewire 170 to the transfer position, whereby the retention device 108 engages the guidewire 170, the guide member 104 can be removed. It is important that the guide member 104 not be removed from the placement catheter 102 prior to complete transfer of the leading portion 164 of the retention device 108 to the guidewire 170, as to do so would render subsequent attempts to engage the retention device 108 with the guidewire 170 difficult. To ensure that the guide member 104 is not prematurely removed from the placement catheter 102, the guide member 104 includes the safety marking 150. As shown in FIG. 15, the safety marking 150 is positioned along the guide member body 144 so that it is visible from the placement catheter 102 only after the distal end 120 of the guide member body 144 is proximal the passage 158 of the drainage catheter 106. As shown in FIG. 15, then, once the safety marking 150 is exposed proximal the placement catheter hub 128, the guide member 104 can be retracted entirely from the placement catheter 102. In other words, because the guidewire 170 has replaced the guide member 104 as the device holding the retention device 108, and therefore the drainage catheter 106, in place relative to the placement catheter 102, the guide member 104 is no longer necessary.

Figure 16:
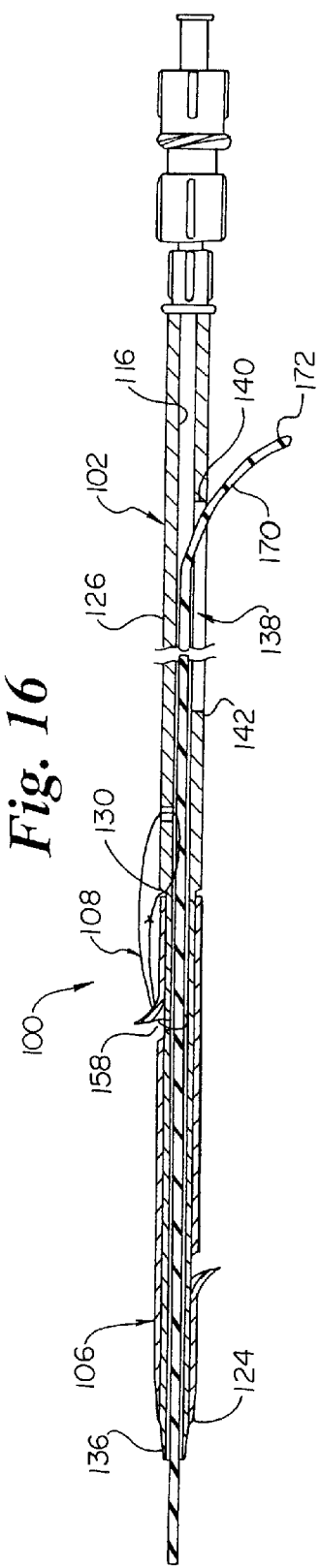
FIG. 16 is a side cross-sectional view of the delivery system of FIG. 14, showing retraction of the guidewire through a push catheter in accordance with the present invention.

With the guide member 104 removed, the delivery system 100 is advanced over the guidewire 170 from the transfer position (FIG. 15) to a delivery position. In a preferred embodiment, as the delivery system is advanced, the proximal end 172 of the guidewire 170 reaches the channel 138 of the placement catheter body 126. As shown in FIG. 16, the proximal end 172 of the guidewire 170 is directed outwardly from the placement catheter lumen 116 via the channel 138. As the guidewire 170 exits the channel 138, the delivery system 100 is advanced into the endoscope (not shown) until the proximal end 172 of the guidewire 170 can be locked to a portion of the endoscope.

With the guidewire 170 now secured, the delivery system 100 is advanced over the guidewire 170 to position the drainage catheter 106 at a desired location in the body cavity. The tapered tip 136 of the placement catheter body 126 extends from the distal end 124 of the drainage catheter 106. The tapered tip 136 facilitates sphincter and stricture entry. Importantly, advancement or forward movement of the placement catheter 102 over the guidewire 170 imparts a similar movement onto the drainage catheter 106 at the abutment surface 130. If retraction of the drainage catheter 106 is required, the placement catheter 102 is simply retracted. Because the retention device 108 is secured to the placement catheter 102, retraction of the placement catheter 102 will cause the retention device 108 to become relatively taut. At this point, the retention device 108 imparts a retraction movement onto the drainage catheter 106 via contact between the retention device 108 and the drainage catheter 106 at the passage 158. Notably, the retention device 108 will slide along the guidewire 170 such that once the retention device 108 is taut, retraction of the placement catheter 102 results in retraction of the drainage catheter 106.

Figure 17:
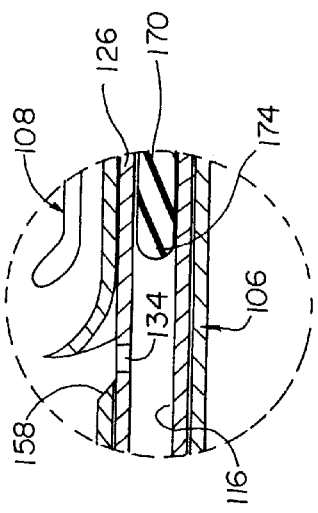
FIG. 17 is a side view of the delivery system of FIG. 14, depicting release of the stent.

Advancement of the delivery system 100 over the guidewire 170 continues until the drainage catheter 106 is positioned at a desired location. The drainage catheter 106 is released from the placement catheter 102 by retracting the guidewire 170. With reference to FIG. 17, retraction of the guidewire 170 results in the distal end 174 of the guidewire 170 entering the placement catheter lumen 116. Once the distal end 174 of the guidewire 170 is approximately proximal the passage 158 in the drainage catheter 106, the retention device 108 is released from the guidewire 170. With this arrangement, the retention device 108 moves freely from the hole 134 in the placement catheter body 126, as well as the passage 158 in the drainage catheter 106. In other words, the retention device 108 no longer secures the drainage catheter 106 to the placement catheter 102, such that the drainage catheter 106 will not retract upon retraction of the placement catheter 102. Thus, with the retention device 108 released, the drainage catheter 106 is deployed.

With the drainage catheter 106 deployed, the placement catheter 102 and/or the guidewire 170 are removed. For example, it may be desirable to maintain placement of the guidewire 170 within the endoscope (not shown) to facilitate further procedures. The channel 138 in the placement catheter 102 provides for rapid exchange of the placement catheter 102. In this regard, the guidewire 170 is radially maneuvered away from the placement catheter 102 through the channel 138, shown in FIG. 16. The placement catheter 102 is retracted over the guidewire 170 to a point where the distal end 142 of the channel 138 is accessible outside of the endoscope (not shown). At this point, the guidewire 170 extends within the placement catheter lumen 116 from the distal end 142 of the channel 138 to the tapered tip 136. Retraction of the placement catheter 102 continues, with the surgeon grasping a portion of the guidewire 170 extending from the channel 138 until the tapered tip 136 is visible outside of the endoscope. The surgeon then grasps the guidewire 170 distal the tapered tip 136 and retracts the placement catheter 102 entirely from the guidewire 170. With this rapid exchange feature, the guidewire 170 can have an overall length much less than twice the length of the placement catheter 102. While the rapid exchange feature has been preferably described as comprising the channel 138 in the placement catheter 102, other configurations, such as providing a single port near the tapered tip 136 of the placement catheter 102, are also acceptable.

Instead of removing only the placement catheter 102, both the placement catheter 102 and the guidewire 170 can be retracted from the endoscope (not shown) simultaneously. In either case, retraction of the placement catheter 102 does not affect placement of drainage catheter 106.

The above-described delivery system 100 is preferably applicable with 10 and 11.5 French drainage catheter systems. It is recognized, however, that other drainage catheter sizes are available. Under certain circumstances, it may be impractical to provide a placement catheter having a distal portion sized to slidably receive a drainage catheter. In other words, as drainage catheter diameter decreases, the outer diameter of the distal portion of the placement catheter must also decrease. At some point, for example with a 7 French drainage catheter inner diameter in conjunction with a standard-sized guidewire, the outer diameter of the distal portion of the placement catheter would require a wall thickness of 0.015 inches. Obviously, this relatively small thickness presents certain manufacturing difficulties. In recognition of this potential obstacle, the present invention envisions a second embodiment in which the guidewire is used to align the placement catheter with the drainage catheter and guide the drainage catheter to the stricture.

Figure 18:
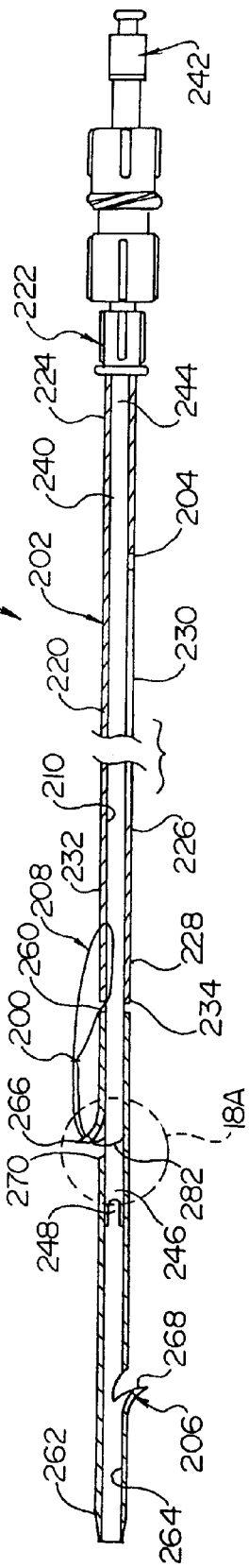
FIG. 18 is a side cross-sectional view of an alternative embodiment of a delivery system in accordance with the present invention.

More particularly, FIG. 18 illustrates an alternative delivery system 200. Similar to the delivery system 100 (FIG. 14), the delivery system 200 includes a placement catheter 202, a guide member 204, a drainage catheter 206 and a retention device 208. The placement catheter 202 includes a placement catheter lumen 210 sized to slidably receive the guide member 204. The guide member 204, in turn, is of a length sufficient to extend distally from the placement catheter 202. Further, the guide member 204 has an outer diameter sized to slidably receive the drainage catheter 206. Finally, the retention device 208 is configured to selectively secure the placement catheter 202 to the drainage catheter 206. Thus, upon final assembly, advancement or distal movement of the placement catheter 202 imparts a distal motion onto the drainage catheter 206. Conversely, retraction or proximal movement of the placement catheter 202 imparts a similar proximal (or retraction) movement onto the drainage catheter 206 via the retention device 208.

The placement catheter 202 includes a placement catheter body 220 and a placement catheter hub 222. The placement catheter lumen 210 extends along the placement catheter body 220 and the placement catheter hub 222. The placement catheter body 220 is defined by a proximal portion 224, an intermediate portion 226 and a distal portion 228. In a preferred embodiment, the intermediate portion 226 of the placement catheter body 220 includes a longitudinally extending channel 230 extending from an outer circumference of the placement catheter body 220 to the placement catheter lumen 210. Finally, the distal portion 228 of the placement catheter body 220 includes an opening 232 to the placement catheter lumen 210, and terminates in an abutment surface 234.

The placement catheter body 220 is preferably formed from a relatively stiff biocompatible polymer via an extrusion process. Alternatively, a biocompatible metal may be used.

The placement catheter hub 222 is similar to that previously described (128 in FIG. 14). Thus, the placement catheter hub 222 is of a type commonly known in the art and is preferably positioned at the proximal portion 224 of the placement catheter body 220.

The guide member 204 includes a guide member body 240 and a guide member hub 242. The guide member body 240 is defined by a proximal end 244 and a distal end 246. As previously described, the guide member body 240 has an outer diameter less a diameter of the placement catheter lumen 210 of the placement catheter 202 such that the guide member body 240 can be slidably received within the placement catheter lumen 210. The distal end 246 of the guide member body 240 forms a tapered pocket 248, described in greater detail below. Additionally, the guide member body 240 includes a safety marking 250 (shown in FIG. 19) placed distal the proximal end 244.

The guide member hub 242 is of a type commonly known in the art and is attached to the proximal end 244 of the guide member body 240.

The guide member body 240 is preferably formed of a relatively rigid biocompatible polymer through an extrusion process. Alternatively, a biocompatible metal may be used. In this regard, the guide member body 240 is solid. Alternatively, the guide member body 240 may be formed to include a central lumen. The guide member body 240 has a length greater than a length of the placement catheter 202. As shown in FIG. 18, then, the length of the guide member body 240 is such that when the guide member 204 is fully extended within the placement catheter 210 (in a loading position), the distal end 246 of the guide member body 240 extends distally from the abutment surface 234 of the placement catheter 202.

The drainage catheter 206 includes a proximal end 260, a distal end 262, a drainage catheter lumen 264, a proximal barb 266 and a distal barb 268. The drainage catheter lumen 264 extends from the proximal end 260 to the distal end 262. The proximal barb 266 extends outwardly in a distal fashion from an outer circumference of the drainage catheter 206. In a preferred embodiment, the proximal barb 266 creates a passage 270 extending from an outer circumference of the drainage catheter 206 to the drainage catheter lumen 264. Similarly, the distal barb 268 extends from an outer circumference of the drainage catheter 206 in a proximal fashion. The proximal barb 266 and the distal barb 268 assist in maintaining position of the drainage catheter 206 within a body cavity. The barbs 266, 268 are opposed to one another to prevent drainage catheter migration in either axial direction.

The drainage catheter lumen 264 is sized to slidably engage a portion of the guide member body 240. In this regard, the drainage catheter lumen 264 has a diameter greater than an outer diameter of the guide member body 240. With reference to FIG. 18, a certain length relationship between the guide member body 240 and the drainage catheter 206 exists in the loading position. In particular, the drainage catheter 206 has a length greater than a length of the portion of the guide member body 240 extending distally from the placement catheter body 220. Importantly, however, the passage 270 must be located along the drainage catheter 206 such that the distal end 246 of the guide member body 240 extends distally past the passage 270, as shown in FIG. 18.

The drainage catheter 206 is preferably formed from a biocompatible, relatively flexible material, such as plastic. Alternatively, a biocompatible metal may be used. The proximal barb 266 and the distal barb 268 are preferably formed in the drainage catheter 206 by imparting properly positioned cuts through the drainage catheter wall.

The retention device 208 is preferably a flexible thread. In one preferred embodiment, the retention device 208 is a biocompatible suture. The suture can be a thread, filament or a wire. Alternatively, the retention device 208 can be a biocompatible wire or cable. Regardless, the retention device 208 preferably extends from a point proximal the abutment surface 234 of the placement catheter 202. As described in greater detail below, the retention device 208 connects the placement catheter 202 to the drainage catheter 206 via the opening 232 in the placement catheter 202 and the passage 270 in the drainage catheter 206.

The delivery system 200 is assembled prior to insertion into the body either by the manufacturer or by the physician by first securing the retention device 208 to the placement catheter 202. In a preferred embodiment, the retention device 208 is a flexible thread having opposing ends. The first end of the flexible thread is passed through the opening 232 in the placement catheter body 220. The first end of the retention device 208 is then maneuvered through the central lumen 210 of the placement catheter 202 and outwardly from the abutment surface 234. The opposing ends of the retention device 208 are then secured to one another, forming a knot 280.

The guide member 204 is then slid within the placement catheter lumen 210. As previously described, the placement catheter lumen 210 has a diameter greater than an outer diameter of the guide member body 240. The distal end 246 of the guide member body 240 is placed within the placement catheter hub 222 and directed toward the distal portion 228 until the distal end 246 of the guide member body 240 extends slightly from the abutment surface 234 of the placement catheter body 220.

The proximal end 260 of the drainage catheter 206 is then coaxially placed over the distal end 246 of the guide member body 240, approximately abutting the abutment surface 234 of the placement catheter body 220. In this regard, the guide member 204 should be positioned relative to the placement catheter 202 such that the distal end 246 of the guide member body 240 extends to a point slightly proximal of the proximal barb 266 of the drainage catheter 206. The retention device 208 is then used to secure the placement catheter 202 to the drainage catheter 206.

The retention device 208 is extended in a distal fashion from the opening 232 of the placement catheter body 220, and through the passage 270 in the drainage catheter 206. More particularly, a loop end or leading end 282 of the retention device 208 is passed into the drainage catheter lumen 264. With the retention device 208 properly positioned relative to the drainage catheter 206, the guide member 204 is advanced through the drainage catheter 206 and over the leading end 282 of the retention device 208, into the loading position shown in FIG. 18. As previously described, the distal end 246 of the guide member body 240 includes a tapered pocket 248 which facilitates sliding of the guide member body 240 over the leading end 282 of the retention device 208.

Figure 18A:
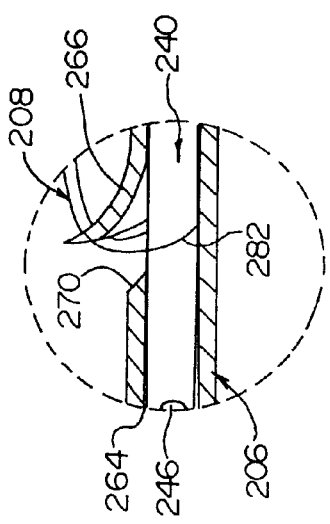
FIG. 18A is an enlarged, side cross-sectional view of a portion of the delivery system of FIG. 18 in accordance with the present invention.

In the loading position (FIG. 18), the guide member hub 242 abuts the placement catheter hub 222, and the distal end 246 of the guide member body 240 extends distally past the passage 270 of the drainage catheter 206 such that the guide member body 240 and the retention device 208 secure the drainage catheter 206 to the placement catheter 202. The guide member hub 242 is locked to the placement catheter hub 222, securing the delivery system 200 in the loading position. Interaction of the retention device 208 and the guide member body 240 is shown in greater detail in FIG. 18A.

Use of the delivery system 200 is basically identical to that previously described with reference to the delivery system 100 (FIGS. 14–17). Generally, the delivery system 200 is pre-assembled as previously described. hi a preferred embodiment, an endoscope is positioned within a body cavity so that a distal end of the endoscope is located near a stricture to be stented or other desired location. A guidewire is maneuvered through the endoscope and positioned such that a distal end of the guidewire is located near the stricture to be stented or other desired location.

Figure 19:
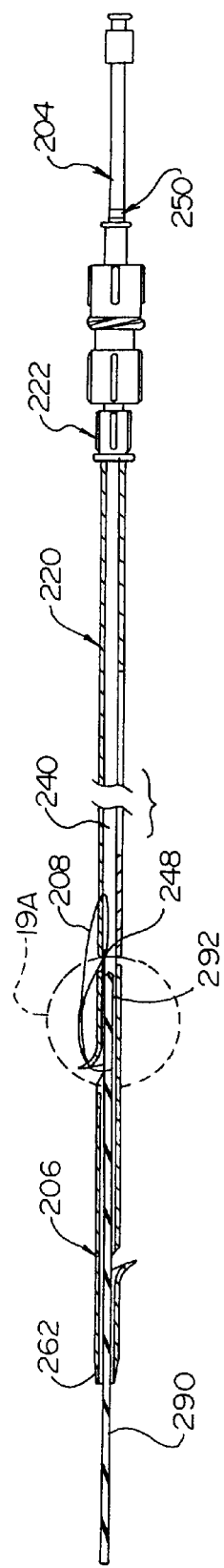
Figure 19A:
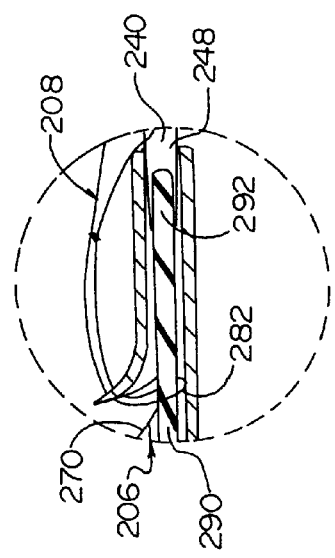

With the endoscope and guidewire in proper position, the guide member hub 242 is released from the placement catheter hub 222. The delivery system 200 is placed over the guidewire 290 and advanced to a transfer position shown in FIG. 19. The guidewire 290 includes a proximal end 292 and a distal end (not shown). The delivery system 200 is loaded onto the guidewire 290 by sliding the distal end 262 of the drainage catheter 206 over the proximal end 292 of the guidewire 290. The delivery system 200 is then slowly advanced over the guidewire 290 such that the proximal end 292 of the guidewire 290 is received within the tapered pocket 248 of the guide member body 240. Continued advancement of the placement catheter 202 and the drainage catheter 206 over the guidewire 290 causes the guide member 204 to retract from the placement catheter 202 via interaction with the guidewire 290. As shown in FIGS. 19 and 19A, as the proximal end 292 of the guidewire 290 moves proximal the passage 270 in the drainage catheter 206, the leading end 282 of the retention device 208 is transferred from the guide member body 240 to the guidewire 290. At a predetermined point of advancement of the placement catheter 202 relative to the guidewire 290, the safety marking 250 (FIG. 19) on the guide member body 240 is visible proximal the placement catheter hub 222. The safety marking 250 indicates that the leading end 282 of the retention device 208 has been fully transferred from the guide member 204 to the guidewire 290. At this point, the user retracts the guide member 204 entirely from the placement catheter 202.

Following removal of the guide member 204, gradual advancement of the placement catheter 202 (and thus, the drainage catheter 206) over the guidewire 290 continues until the proximal end 292 of the guidewire 290 is accessible through the channel 230 in the placement catheter body 220, as shown in FIG. 20. The proximal end 292 of the guidewire 290 is directed radially from the placement catheter lumen 210 via the channel 230 as the placement catheter 202 is continually advanced over the guidewire 290 until the guidewire 290 can be locked onto the endoscope (not shown) via standard methods.

With the guidewire 290 now secure, the delivery system 200 is advanced over the guidewire 290 until the drainage catheter 206 is positioned at the desired location in the body. The drainage catheter 206 is released by retracting the guidewire 290 until the distal end 294 of the guidewire 290 clears the leading end 282 of the retention device 208, as shown in FIG. 21. In this drainage catheter delivery position, the retention device 208 no longer connects the drainage catheter 206 to the placement catheter 202.

With the drainage catheter 206 properly positioned, the placement catheter 202 can be retracted over the guidewire 290 and through the endoscope (not shown). In this regard, the channel 230 facilitates rapid exchange of the placement catheter 202 as previously described. The guidewire 290 can then be used with additional procedures. Alternatively, the guidewire 290 can be removed from the endoscope. Even further, the placement catheter 202 and the guidewire 290 may be removed simultaneously.

The delivery systems 100 and 200 have been described with reference to use within an endoscope, accommodating a variety of drainage catheter sizes. Additionally, it is recognized that different procedures require variations in endoscope diameter as well. This variation in endoscope diameter may present certain concerns where the placement catheter (102 and 202) includes the channel (138 and 230) for rapid exchange capabilities.

The relationship between placement catheter diameter and endoscope diameter is shown, for example, in FIGS. 22A and 22B. FIG. 22A presents a cross-sectional view of a placement catheter 300 within an endoscope 302. The placement catheter 300 defines a placement catheter lumen 304 and includes a channel 306. The channel 306 is appropriately sized to allow passage of a guidewire 308 into and out of the placement catheter lumen 304. In particular, the channel 306 is sized to have a width greater than a diameter of the guidewire 308.

The endoscope 302 includes an endoscope lumen 310 within which the placement catheter 300 and the guidewire 308 are disposed. The endoscope lumen 310 is sufficiently small to prevent the guidewire 308 from entirely disengaging the placement catheter 300. In other words, where the endoscope lumen 310 has a diameter less than the placement catheter 300 diameter and half of the guidewire 308 diameter, undesired movement of the guidewire 308 from the placement catheter 300 is prevented.

A different relationship is depicted in FIG. 22B. The same placement catheter 300, including the placement catheter lumen 304 and the channel 306, is once again shown. Additionally, the guidewire 308 is identical. However, an endoscope 312 having an enlarged endoscope lumen 314 is shown. The endoscope lumen 314 of FIG. 22B is too large to maintain the guidewire 308 within the channel 306. In other words, it may be possible for the guidewire 308 to exit entirely from the channel 306 and freely move about an outer circumference of the placement catheter 300. This situation may possibly restrict movement of the placement catheter 300 within the endoscope 312 as the guidewire 308 becomes lodged between the outer circumference of the placement catheter 300 and the endoscope 312.

In light of the potential concerns presented by oversized endoscopes, a preferred embodiment of the present invention provides for a sheath 320 shown in FIG. 23. The sheath 320 includes a hub assembly 322 and a sheath body 324. The hub assembly 322 includes a proximal hub 326 and a distal hub 328. The sheath body 324 is attached to, and extends distally from, the distal hub 328.

The hub assembly 322 is of a type commonly known in the art and includes the proximal hub 326 and the distal hub 328. The proximal hub 326 is rotatably secured to the distal hub 328. Further, the proximal hub 326 and the distal hub 328 include a slot 330. With this configuration, the proximal hub 326 can be rotated relative to the distal hub 328 such that the slots 330 are aligned. Conversely, the proximal hub 326 can be rotated relative to the distal hub 328 such that the slots 330 are no longer aligned.

The sheath body 324 includes a proximal end 332 and a distal end 324, and defines a sheath lumen 336. Additionally, the sheath body 324 includes a longitudinally extending slit 338. The slit 338 extends from the proximal end 332 to the distal end 334. As shown in FIG. 23A, the slit 338 extends from an outer circumference of the sheath body 324 to the sheath lumen 336. The slit 338, while normally closed, can be forcibly expanded to allow a guidewire (not shown) to move radially, or "peel away", from the sheath lumen 336.

With reference to FIGS. 14 and 23, the sheath 320 is sized to be coaxially received over the placement catheter body 126 such that the sheath body 324 encompasses the channel 136 of the placement catheter body 126. In this regard, the sheath lumen 336 has a diameter slightly greater than an outer diameter of the placement catheter body 126. The hub assembly 322 is preferably positioned distal the distal end 142 of the channel 138. The slots 330 in the hub assembly 322 and the slit 338 in the sheath body 324 are aligned with the channel 138.

During use, the delivery system 100, including the sheath 320, is assembled as previously described and advanced over the guidewire 170 (FIG. 15). As the placement catheter 102 is advanced such that a portion of the guidewire 170 is adjacent the channel 138 of the placement catheter body 126, the sheath body 324 serves to maintain engagement between the placement catheter 102 and the guidewire 170.

As the placement catheter 102 is advanced to a point whereby the proximal end 172 of the guidewire 170 is near the distal end 142 of the channel 138, the proximal end 172 of the guidewire 170 is maneuvered through the slots 330 in the hub assembly 322. If desired, the proximal hub 326 can be rotated relative to the distal hub 328 so as to secure the guidewire 170 within the hub assembly 322.

Rapid exchange of the placement catheter 102 relative to the guidewire 170, as previously described, is facilitated by the sheath 320. In particular, the hub assembly 322 is arranged such that the slots 330 in the proximal hub 326 and the distal hub 328 are aligned. The placement catheter 102 and the guidewire 170 can then be maneuvered such that the guidewire 170 is moved radially from the channel 138 and through the slit 338 in the sheath body 324. Exchange of the placement catheter 102 relative to the guidewire 170 can then take place as previously described.

While the sheath 320 has been described as including a slit 338 in the sheath body 324, other configurations are acceptable. For example, as shown in FIG. 23B, a sheath body 340 can be configured to form a flap. The sheath body 340 includes a wall defined by a first end 342 and a second end 344. The first end 342 overlaps the second end 344. The overlap design is normally closed. However, when desired, a guidewire (not shown) can be removed from within the sheath body 340 by sliding the guidewire between the first end 342 and the second end 344 and then radially away from the sheath body 340.

Yet a further alternative delivery system 400 is shown in FIG. 24. Except as described herein, the delivery system 400 is substantially the same in form and function as delivery system 100 described with referenced to FIG. 14. The delivery system 400 includes a push or placement catheter 402, a guide member 404, a stent or drainage catheter 406, and a retention device 408. The retention device 408 releasably connects a distal portion of the placement catheter 402 to a proximal portion of the drainage catheter 406. The retention mechanism 408 is substantially the same as retention mechanism 28 discussed with reference to delivery system 20 and retention mechanism 108 discussed with reference to delivery system 100. Both the drainage catheter 406 and the placement catheter 402 are disposed about the guide member 404.

FIG. 25 illustrates the placement catheter 402 for use in delivery system 400. Push or placement catheter 402 includes a distal tubular portion 410, a proximal tubular portion 412, and a proximal fitting 414. Distal tubular portion 410 has a circular single-wall cross-section as illustrated in FIG. 28. Similarly, proximal tubular portion 412 has a circular single-wall cross-section as illustrated in FIG. 29. The distal and proximal tubular portions 410, 412 may be formed of a single extrusion or may be formed of separate components connected together. In either case, the placement catheter 402 defines a catheter lumen 418 extending through the proximal portion 412 and the distal portion 410. A proximal guidewire port 416 is disposed at the proximal end of the distal tubular portion 410. The distal tubular portion 410 also includes a distal port 417. The proximal guidewire port 416 provides access from the exterior of the placement catheter 402 to the catheter lumen 418 therein. A ramp (not shown) may be provided in the catheter lumen 418 adjacent the proximal guidewire port 416 in order to smoothly guide the guidewire (not shown) exiting the proximal guidewire port 432 into the proximal guidewire port 416.

The proximal fitting 414 comprises a standard Tuohy-Borst fitting 413 and may optionally include a strain relief 415. The proximal fitting 414 serves to form a fluid tight seal between the placement catheter 402 and the proximal portion of the guide member 404. In addition, a reduced diameter portion (not shown) may be disposed inside the catheter lumen 418 adjacent the proximal fitting 414 to engage a stop means 420 disposed on the proximal end of the guide member 404 as best seen in FIG. 26. The reduced diameter portion of the catheter lumen 418 may comprise a shorter hypotube section disposed in the proximal portion of the catheter lumen 418 adjacent the proximal fitting 414. The stop means 420 has a diameter slightly larger than the reduced diameter portion, such that the stop means 420 may not pass proximally through the reduced diameter portion, thereby limiting proximal displacement of the guide member 404 relative to the placement catheter 402. Specifically, stop means 420 prevents the proximal guidewire port 432 of the guide member 404 from engaging the proximal guidewire port 416 of the placement catheter 402 in order to prevent the guidewire (not shown) from jamming between the proximal guidewire ports 432, 416.

FIG. 26 illustrates the guide member 404 for use in the delivery system 400. Guide member 404 includes a distal tubular portion 422 and a proximal wire portion 424. The distal portion 422 has a single-wall circular cross-section as illustrated in FIG. 27 to define a guidewire lumen 430 therein. The distal tubular portion 422 includes a proximal guidewire port 432 and a distal guidewire port 434. Proximal guidewire port 432 is located distal of the proximal end of the guide member 404.

A handle 426 is disposed on the proximal end of the wire portion 424 to facilitate manipulation of the guide member 404. Although illustrated as a solid wire, the proximal portion 424 may comprise any suitable structure, such as a metallic tube or reinforced polymer tube, which transfers longitudinal force to the distal tubular portion 422. Preferably, the proximal portion 424 comprises a solid wire having a circular cross-section as illustrated in FIG. 30. The distal end of the proximal wire portion 424 is rigidly connected to the proximal end of the distal tubular portion 422 by a radiopaque metal band or coil 428 or by other suitable means.

The distal tubular portion 422 is sized to fit in the catheter lumen 418 in the distal portion 410 of the placement catheter 402. In addition, the distal tubular portion 422 of the guide member 404 has a length slightly longer than the length of the drainage catheter 406, and preferably approximately fourteen (14) cm greater than the length of the drainage catheter 406. The distal portion 410 of the placement catheter 402 is preferably slightly longer than the distal portion 422 of the guide member 404, and preferably approximately five (5) cm longer than the distal portion 422. The stop means 420 is positioned on the proximal wire portion 424 of the guide member 404 to prevent the proximal end of the distal tubular portion 422 from engaging the proximal end of the distal tubular portion 410 of the placement catheter 402 adjacent the proximal guidewire port 416.

Refer now to FIG. 31, which illustrates the delivery system 400 disposed on a guidewire 500. The hidden portions of the guidewire 500, guide member 404, and retention device 408 are shown by hidden (dashed) lines. As can be seen from the assembly drawing of delivery system 400 illustrated in FIG. 31 and the various cross-sectional views shown in FIGS. 32–36, the guidewire 500 extends into the guidewire lumen 430 of the distal tubular portion 422 of the guide member 404 by way of distal guidewire port 434. The guidewire 500 exits the distal tubular portion 422 of the guide member 404 through proximal guidewire port 432. From the proximal guidewire port 432, the guidewire 500 extends through the catheter lumen 418 of the distal tubular portion 410 of the placement catheter 402. The guidewire 500 is guided into the proximal guidewire port 416 by a ramp (not shown) in the catheter lumen 418 adjacent the proximal guidewire port 416. From the proximal guidewire port 416, the guidewire 500 extends substantially parallel with the placement catheter 402 to a point adjacent the proximal fitting 414.

The distal tubular portion 422 of the guide member 404 extends into the lumen 407 of the drainage catheter 406 and into the catheter lumen 418 of the distal tubular portion 410 of the placement catheter 402. The proximal wire portion 424 of the guide member 404 extends from the proximal end of the distal tubular portion 422 through the catheter lumen 418 in the proximal tubular portion 412. The proximal wire portion 424 extends out the proximal end of the proximal fitting 414 and is rigidly connected to the handle 426.

Figure 37C:
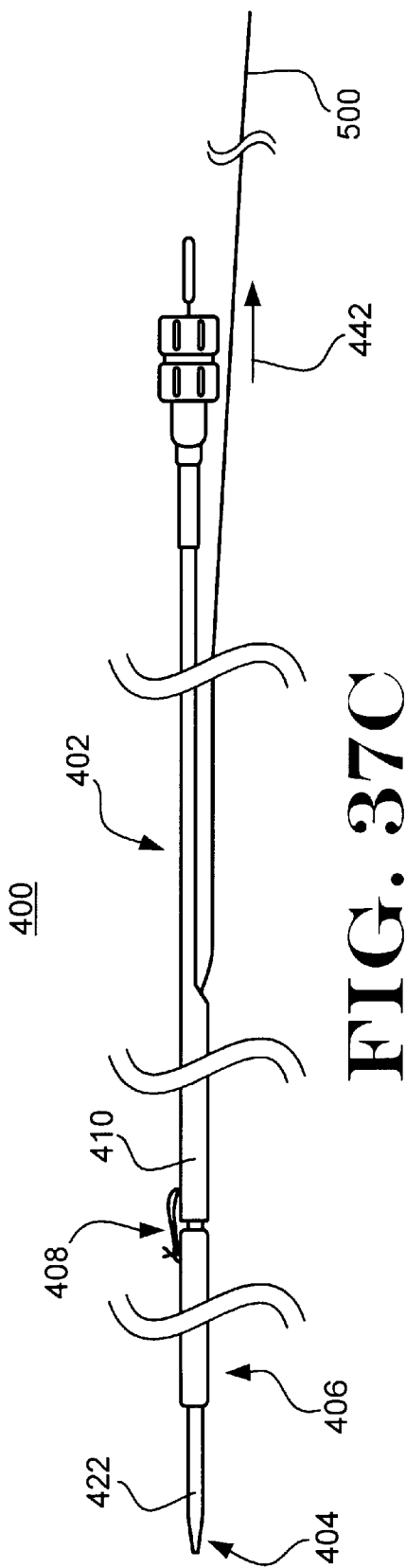
Figure 37D:
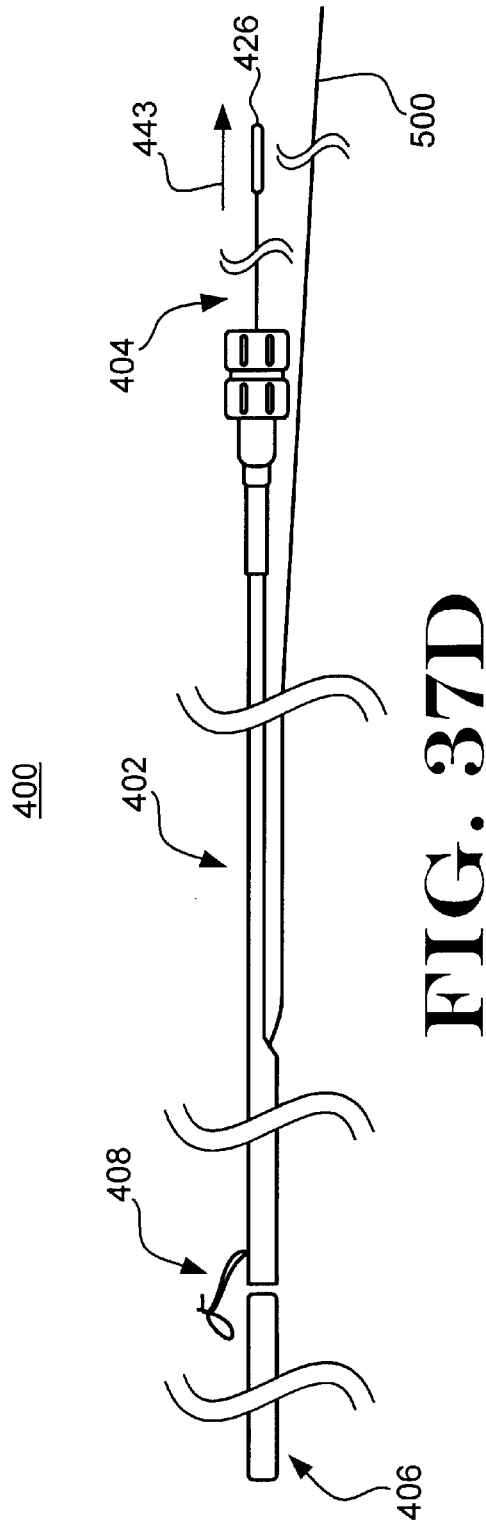

Refer now to FIGS. 37A–37D, which illustrate a method of using the delivery system 400. In particular, FIGS. 37A–37D illustrate a "wire first" technique, wherein the guidewire 500 is inserted into the desired duct of the patient prior to inserting the delivery system 400. FIG. 37A illustrates advancement of the delivery system 400 over the guidewire 500 as indicated by arrow 440. FIG. 37B illustrates the delivery system 400 completely advanced over the guidewire 500, with the drainage catheter 406 properly positioned at the desired site for deployment. FIG. 37C illustrates retraction of the guidewire 500, and FIG. 37D illustrates retraction of the guide member 404, thereby releasing drainage catheter 406 from retention device 408.

Those skilled in the art will recognize that the order of insertion may be modified to suit the particular clinical situation. For example, the guidewire 500 and the delivery system 400 may be inserted into the patient simultaneously.

With the wire first technique, the guidewire 500 is navigated through the patient's duct system to the desired treatment site. Once the distal end of the guidewire 500 has been positioned adjacent the desired treatment site, the delivery system 400 maybe advanced over the guidewire 500. To advance the delivery system 400, the proximal end of the guidewire 500 is inserted into the distal guidewire port 434 of the guide member 404. The delivery system 400 is then advanced over the guidewire 500 until the proximal end of the guidewire engages the ramp (not shown) and exits the proximal guidewire port 416 of the placement catheter 402. While the delivery system 400 is being advanced over the guidewire 500, the treating physician may maintain position of the guidewire 500 by grasping the guidewire immediately adjacent the distal end of the delivery system 400. Once the guidewire 500 exits the proximal guidewire port 416, the treating physician may maintain position of the guidewire 500 by grasping the exited guidewire 500 proximal of the guidewire port 416. A discussed with reference to delivery systems 20, 100, and 200, the delivery system 400 may be advanced or retracted along the guidewire 500 to fine tune the position of the drainage catheter 406 inside the patient's duct system. Once the delivery system 400 has been advanced or retracted over the guidewire 500 such that the drainage catheter 406 is in the desired deployment position, the guidewire 500 may be retracted as indicated by arrow 442 in FIG. 37C. Preferably, the guidewire 500 is retracted in the proximal direction a sufficient distance such that the distal end of the guidewire 500 is positioned proximal of the drainage catheter 406 inside the catheter lumen 418 of the distal tubular portion 410 of the placement catheter 402. Alternatively, the guidewire 500 maybe retracted in the proximal direction as indicated by arrow 442 a sufficient distance to position the distal end of the guidewire within the distal tubular portion 422 of the guide member 404. With either arrangement, the drainage catheter 406 may be deployed without interference from the guidewire 500. Maintaining the distal end of the guidewire within the distal tubular portion 422 of the guide member 404, or the distal tubular portion 410 of the placement catheter 402, allows the guidewire 500 to be re-advanced in the distal direction if it becomes necessary to reposition the delivery system 400 in the patient's duct system. Once the guidewire 500 has been retracted in the proximal direction a sufficient direction as discussed above, the guide member 404 is then retracted in the proximal direction as indicated by arrow 443 illustrated in FIG. 37D. The guide member 404 may be retracted by pulling on the handle 426. If the guidewire 500 has been retracted a sufficient distance such that the distal end of the guidewire 500 is in the distal tubular portion 410 of the placement catheter 402, the guide member 404 may be retracted in the proximal direction while holding guidewire 500 in a fixed position. Alternatively, if the guidewire 500 has only been retracted a sufficient distance such that the distal end of the guidewire is in the distal tubular portion 422 of the guide member 404, the guide member 404 and the guidewire 500 must be retracted together in the proximal direction as indicated by arrow 443. Under either circumstance, the distal tubular portion 422 of the guide member 404 is retracted a sufficient distance to release the drainage catheter 406 from the retention device 408 as described in detail with reference to delivery system 20, 100, and 200. Once the drainage catheter 406 has been released by the proximal displacement of the guide member 404, the delivery system 400 (excluding the drainage catheter 406) and the guidewire 500 may be withdrawn from the patient. Alternatively, the delivery system (excluding the drainage catheter 406) may be retracted along the guidewire 500 while maintaining the position of the guidewire 500 in the patient's duct system. This latter method may be used, for example, to subsequently advance other devices over the guidewire 500 to the desired treatment site in the patient's duct system.

Those skilled in the art will recognize that the present invention maybe manifested in a wide variety of forms other than the specific embodiments described and contemplated herein. Accordingly, departures in form and detail may be made without departing from the scope and spirit of the present invention as described in the appended claims.

What is claimed is:

1. A drainage catheter delivery system comprising:
   a guide member having a proximal end, a distal end and a guidewire lumen extending therethrough, the guidewire lumen having a proximal port located distal of the proximal end of the guide member;
   a placement catheter having a proximal end, a distal end, and a catheter lumen extending therethrough, the catheter lumen having a proximal port located distal of the proximal end of the placement catheter, the placement catheter disposed over the guide member and longitudinally movable relative thereto; and
   a drainage catheter disposed about the guide member distal of the placement catheter.

2. A drainage catheter delivery system as in claim 1, further comprising a means for releasably connecting the placement catheter to the drainage catheter.

3. A drainage catheter delivery system as in claim 2, wherein the guide member includes a proximal portion and a distal portion, the proximal portion of the guide member including a stop mechanism which limits proximal displacement of the guide member relative to the placement catheter.

4. A drainage catheter delivery system as in claim 3, wherein the distal portion of the guide member comprises a tube.

5. A drainage catheter delivery system as in claim 4, wherein the drainage catheter is disposed about the distal tubular portion of the guide member.

6. A drainage catheter delivery system as in claim 5, wherein the proximal portion of the guide member has a lower profile than the distal portion of the guide member.

7. A drainage catheter delivery system as in claim 6, wherein the proximal portion of the guide member comprises a wire.

8. A drainage catheter delivery system as in claim 7, wherein the placement catheter includes a proximal portion and a distal portion, and wherein the distal portion of the placement catheter comprises a tube.

9. A drainage catheter delivery system as in claim 8, wherein the distal portion of the guide member is disposed in the distal tube portion of the placement catheter.

10. A drainage catheter delivery system as in claim 9, wherein the proximal portion of the placement catheter has a lower profile than the distal portion of the placement catheter.

11. A drainage catheter delivery system as in claim 10, wherein the proximal portion of the placement catheter comprises a tube.

12. A drainage catheter delivery system as in claim 11, wherein the proximal portion of the guide member is disposed in the proximal tube portion of the placement catheter.

13. A drainage catheter delivery system as in claim 12, wherein the distal portion of the placement catheter is longer than the distal portion of the guide member.

14. A drainage catheter delivery system as in claim 13, wherein the proximal portion of the placement catheter is shorter than the proximal portion of the guide member.

15. A delivery system as in claim 2, wherein the releasable connecting means disconnects the drainage catheter upon displacement of the guide member.

16. A delivery system as in claim 15, wherein the displacement is longitudinal.

17. A delivery system as in claim 16, wherein the displacement is in a proximal direction.

18. A delivery system as in claim 17, wherein the releasable connecting means comprises a tying mechanism.

19. A delivery system as in claim 18, wherein the tying mechanism comprises a flexible thread.

20. A delivery system as in claim 19, wherein the flexible thread passes through a passage in the drainage catheter.

21. A delivery system as in claim 20, wherein the flexible thread passes through a passage in the placement catheter.

22. A delivery system as in claim 21, wherein the flexible thread forms a loop around the distal portion of the guide member disposed in the drainage catheter.

23. A delivery system as in claim 22, wherein the loop passes through the passage in the drainage catheter.

* * * * *